US007858367B2

(12) United States Patent
Amalfitano et al.

(10) Patent No.: US 7,858,367 B2
(45) Date of Patent: Dec. 28, 2010

(54) VIRAL VECTORS AND METHODS FOR PRODUCING AND USING THE SAME

(75) Inventors: Andrea Amalfitano, Durham, NC (US); Dwight D. Koeberl, Durham, NC (US); Baodong Sun, Morrisville, NC (US)

(73) Assignee: Duke University, Durham, NC (US)

(*) Notice: Subject to any disclaimer, the term of this patent is extended or adjusted under 35 U.S.C. 154(b) by 376 days.

(21) Appl. No.: 10/511,980

(22) PCT Filed: Apr. 30, 2003

(86) PCT No.: PCT/US03/13323

§ 371 (c)(1),
(2), (4) Date: Apr. 7, 2005

(87) PCT Pub. No.: WO03/092594

PCT Pub. Date: Nov. 13, 2003

(65) Prior Publication Data

US 2005/0220766 A1 Oct. 6, 2005

Related U.S. Application Data

(60) Provisional application No. 60/376,397, filed on Apr. 30, 2002.

(51) Int. Cl.
C12N 15/00 (2006.01)
C12N 7/00 (2006.01)
A61K 48/00 (2006.01)
(52) U.S. Cl. .................. 435/320.1; 435/235.1; 424/93.2
(58) Field of Classification Search ........................ None
See application file for complete search history.

(56) References Cited

U.S. PATENT DOCUMENTS

| | | | |
|---|---|---|---|
| 4,501,729 A | 2/1985 | Boucher et al. | |
| 4,968,603 A | 11/1990 | Slamon et al. | |
| 5,399,346 A | 3/1995 | Anderson et al. | |
| 5,521,291 A | 5/1996 | Curiel et al. | |
| 5,712,136 A | 1/1998 | Wickham et al. | |
| 5,770,442 A | 6/1998 | Wickham et al. | |
| 5,858,351 A | 1/1999 | Podsakoff et al. | |
| 5,861,156 A | 1/1999 | George et al. | |
| 5,869,248 A | 2/1999 | Yuan et al. | |
| 5,871,982 A | 2/1999 | Wilson et al. | |
| 5,872,005 A | 2/1999 | Wang et al. | |
| 5,877,022 A | 3/1999 | Stinchcomb et al. | |
| 5,922,315 A | 7/1999 | Roy et al. | |
| 5,962,313 A * | 10/1999 | Podsakoff et al. ......... | 435/320.1 |
| 6,013,487 A | 1/2000 | Mitchell | |
| 6,083,702 A | 7/2000 | Mitchell et al. | |
| 6,156,303 A | 12/2000 | Russell et al. | |
| 6,251,677 B1 | 6/2001 | Wilson et al. | |
| 6,258,595 B1 | 7/2001 | Gao et al. | |
| 6,270,996 B1 | 8/2001 | Wilson et al. | |
| 6,294,370 B1 | 9/2001 | Bogedain et al. | |
| 6,329,181 B1 | 12/2001 | Xiao et al. | |
| 6,329,958 B1 | 12/2001 | McLean et al. | |
| 6,383,794 B1 * | 5/2002 | Mountz et al. ............. | 435/235.1 |
| 2003/0017139 A1 * | 1/2003 | Souza et al. ............... | 424/93.2 |

FOREIGN PATENT DOCUMENTS

| | | |
|---|---|---|
| WO | WO90/05142 | 5/1990 |
| WO | WO 00/11149 | 3/2000 |
| WO | WO 02/063025 | 8/2002 |

OTHER PUBLICATIONS

Lieber et al. J. Virol. 73(11):9314-9324; 1999.*
Samulski et al. J. Virol. 63(9):3822-3828; 1989.*
Lieber et al., Integrating Adenovirus-Adeno-Associated Virus Hybrid Vectors Devoid of all Viral Genes, *J. of Virology* 73(11):9314-9324 (Nov. 1999).
Pauley et al., Intercellular Transfer of the Virally Derived Precursor Form of Acid α-Glucosidase Corrects the Enzyme Deficiency in Inherited Cardioskelatal Myopathy Pompe Disease, *Human Gene Therapy* 12:527-538 (Mar. 20, 2001).
Ding et al., Long-Term Efficacy after [E1, polymerase] Adenovirus-Mediated Transfer of Human Acid-α-Glucosidase Gene into Glycogen Storage Disease Type II Knockout Mice, *Human Gene Therapy* 12:955-965 (May 20, 2001).
Sun et al., Long-Term Correction of Glycogen Storage Disease Type II with a Hybrid Ad-AAV Vector, *Molecular Therapy* 7(2):193-201 (Feb. 2003).
Notification of Transmittal of the International Search Report for PCT/US03/13323 dated Aug. 2, 2004.
Written Opinion for PCT/US03/13323 dated Oct. 19, 2004.
International Preliminary Examination Report corresponding to PCT App. No. PCT/US03/13323 dated Apr. 7, 2005.
Allen et al., "Improved Adeno-Associated Virus Vector Production with Transfection of a Single Helper Adenovirus Gene, E4*orf*6," Mol. Ther., vol. 1, pp. 88-95 (2000).
Amalfitano et al., "Production and Characterization of Improved Adenovirus Vectors with the E1, E2b, and E3 Genes Deleted," J. Virol., vol. 72, pp. 926-933 (1998).

(Continued)

*Primary Examiner*—Fereydoun G Sajjadi
(74) *Attorney, Agent, or Firm*—Jenkins, Wilson, Taylor & Hunt, P.A.

(57) ABSTRACT

A recombinant hybrid virus which includes: (a) a deleted adenovirus vector genome having the adenovirus 5' and 3' cis-elements for viral replication and encapsidation and a deletion in an adenovirus genomic region selected from the polymerase region and/or the preterminal protein region, wherein the deletion essentially prevents the expression of a functional polymerase and/or preterminal protein from the deleted region and the hybrid virus does not otherwise express a functional polymerase protein; and (b) a recombinant adeno-associated virus (AAV) vector genome flanked by the adenovirus vector genome sequences of (a), wherein the recombinant AAV vector genome includes an AAV packaging sequence and a heterologous nucleic acid sequence, wherein the heterologous nucleic acid sequence is flanked by 5' and 3' AAV inverted terminal repeats.

58 Claims, 8 Drawing Sheets

OTHER PUBLICATIONS

Amalfitano et al., "Systemic correction of the muscle disorder glycogen storage disease type II after hepatic targeting of a modified adenovirus vector encoding human acid-α-glucosidase," PNAS, vol. 96, pp. 8861-8866 (1999).
Gao et al., "High-Titer Adeno-Associated Viral Vectors from a Rep/Cap Cell Line and Hybrid Shuttle Virus," Hum. Gene Ther., vol. 9, pp. 2353-2362 (1998).
Gao et al., "Rep/Cap Gene Amplification and High-Yield Production of AAV in an A549 Cell Line Expressing Rep/Cap," Mol. Ther., vol. 5, pp. 644-649 (2002).
He et al., "A simplified system for generating recombinant adenoviruses," PNAS, vol. 95, pp. 2509-2514 (1998).
Hodges et al., "Multiply deleted [E1, polymerase-, and pTP-] adenovirus vector persists despite deletion of the preterminal protein," J. Gene Med., vol. 2, pp. 250-259 (2000).
Lieber et al., "Recombinant Adenoviruses with Large Deletions Generated by Cre-Mediated Excision Exhibit Different Biological Properties Compared with First-Generation Vectors In Vitro and In Vivo," J. Virol., vol. 70, pp. 8944-8960 (1996).
Liu et al., "Production of recombinant adeno-associated virus vectors using a packaging cell line and a hybrid recombinant adenovirus," Gene Ther., vol. 6, pp. 293-299 (1999).
Muzyczka, N., "Use of adeno-associated virus as a general transduction vector for mammalian cells," Current Topics in Microbiology and Immunology, vol. 158, pp. 97-129 (1992).
Sun et al., "Packaging of an AAV Vector Encoding Human Acid α-Glucosidase for Gene Therapy in Glycogen Storage Disease Type II with a Modified Hybrid Adenovirus-AAV Vector," Mol. Ther., vol. 7, pp. 467-477 (2003).
Van Hove et al., "High-level production of recombinant human lysosomal acid a-glucosidase in Chinese hamster ovary cells which targets to heart muscle and corrects glycogen accumulation in fibroblasts from patients with Pompe disease," PNAS, vol. 93, pp. 65-70 (1996).
Weitzman et al., "Recruitment of wild-type and recombinant adeno-associated virus into adenovirus replication centers," J. Virol., vol. 70, No. 3, pp. 1845-1854 (1996).
Zhang et al., "Recombinant adenovirus expressing adeno-associtated virus cap and rep proteins supports production of high-titer recombinant adeno-associated virus," Gene Ther., vol. 8, pp. 704-712 (2001).
Allen et al., "Identification and Elimination of Replication-Competent Adeno-Associated Virus (AAV) That Can Arise by Nonhomologous Recombination during AAV Vector Production," Journal of Virology. vol. 71, No. 9 pp. 6816-6822 (1997).
Conway et al., "High-titer recombinant adeno-associated virus production utilizing a recombinant herpes simplex virus type I vector expressing AAV-2 Rep and Cap," Gene Therapy. vol. 6 pp. 986-993 (1999).
Coulie et al., "A New Gene Coding for a Differentiation Antigen Recognized by Autologous Cytolytic T Lymphocytes on HLA-A2 Melanomas," Journal of Experimental Medicine. vol. 180 pp. 35-42 (1994).
Daly et al., "Neonatal gene transfer leads to widespread correction of pathology in a murine model of lysosomal storage disease," PNAS. vol. 96 pp. 2296-2300 (1999).
Franco et al., "Evasion of Immune Response to Introduced Human Acid α-Glucosidase by Liver-Restricted Expression in Glycogen Storage Disease Type II," Molecular Therapy. vol. 12, No. 5 pp. 876-884 (2005).
Gorman et al., "Stable alteration of pre-mRNA splicing patterns by modified U7 small nuclear RNAs," PNAS. vol. 95 pp. 4929-4934 (1998).
Hoefsloot et al., "Primary structure and processing of lysosomal α-glucosidase; homology with the intestinal sucrase—isomaltase complex," The EMBO Journal. vol. 7, No. 6 pp. 1697-1704 (1988).
Inoue, N., and Russell, D.W., "Packaging Cells Based on Inducible Gene Amplification for the Production of Adeno-Associated Virus Vectors," Journal of Virology. vol. 72, No. 9 pp. 7024-7031 (1998).
Jung et al., "Adeno-associated viral vector-mediated gene transfer results in long-term enzymatic and functional correction in multiple organs of Fabry mice," PNAS. vol. 98, No. 5 pp. 2676-2681 (2001).
Kawakami et al., "Cloning of the gene coding for a shared human melanoma antigen recognized by autologous T cells infiltrating into tumor," PNAS. vol. 91 pp. 3515-3519 (1994).
Kawakami et al., "Identification of the Immunodominant Peptides of the MART-1 Human Melanoma Antigen Recognized by the Marjority of HLA-A2-restricted Tumor Infiltrating Lymphocytes," The Journal of Experimental Medicine. vol. 180 pp. 347-352 (1994).
Kishnani et al., "Canine Model and Genomic Structural Organization of Glycogen Storage Disease Type la (GSD la)," Vet. Pathol. vol. 38 pp. 83-91 (2001).
Matsushita et al., "Adeno-associated virus vectors can be efficiently produced without helper virus," Gene Therapy. vol. 5 pp. 938-945 (1998).
Raben et al., "Targeted Disruption of the Acid α-Glucosidase Gene in Mice Causes an Illness with Critical Features of Both Infantile and Adult Human Glycogen Storage Disease Type II," The Journal of Biological Chemistry. vol. 273, No. 30 pp. 19086-19092 (1998).
Recchia et al., "Site-specific integration mediated by a hybrid adenovirus/adeno-associated virus vector," PNAS. vol. 96 pp. 2615-2620 (1999).
Robbins et al., "Recognition of Tyrosinase by Tumor-infiltrating Lymphocytes from a Patient Responding to Immunotherapy," Cancer Research. vol. 54 pp. 3124-3126 (1994).
Rosenberg, "A New Era for Cancer Immunotherapy Based on the Genes that Encode Cancer Antigens," Immunity. vol. 10 pp. 281-287 (1999).
Rouet et al., "A Potent Enhance Made of Clustered Liver-specific Elements in the Transcription Control Sequences of Human α1-Microglobulin/Bikunin Gene," The Journal of Biological Chemistry. vol. 267, No. 29 pp. 20765-20773 (1992).
Snyder et al., "Correction of hemophilia B in canine and murine models using recombinant adeno-associated viral vectors," Nature Medicine. vol. 5, No. 1 pp. 64-70 (1999).
Tinsley et al., "Amelioration of the dystrophic phenotype of *mdx* mice using a truncated utrophin transgene," Letters to Nature. vol. 384 pp. 349-353(1996).
Van der Ploeg et al., "Intravenous Administration of Phosphorylated Acid α-Glucosidase Leads to Uptake of Enzyme in Heart and Skeletal Muscle of Mice," Journal of Clinical Investigation. vol. 87 pp. 513-518 (1991).
Vincent et al., "Long-term correction of mouse dystrophic degeneration by adenovirus-mediated transfer of a minidystrophin gene," Nature Genetics. vol. 5 pp. 130-134 (1993).
Wang et al., "Sustained correction of bleeding disorder in hemophilia B mice by gene therapy," PNAS. vol. 96 pp. 3906-3910 (1999).
Wisselaar et al., "Structural and Functional Changes of Lysosomal Acid -Glucosidase during Intracellular Transport and Maturation," The Journal of Biological Chemistry. vol. 268, No. 3 pp. 2223-2231 (1993).
Xiao et al., "Adeno-Associated Virus as a Vector for Liver-Directed Gene Therapy," Journal of Virology. vol. 72, No. 12 pp. 10222-10226 (1998).
Yang et al., "Characterization of Cell Lines That Inducibly Express the Adeno-Associated Virus Rep Proteins," Journal of Virology. vol. 68, No. 8 pp. 4847-4856 (1994).
Zolotukhin et al., "Recombinant adeno-associated virus purification using novel methods improves infectious titer and yield," Gene Therapy. vol. 6 pp. 973-985 (1999).
Sun et al., Correction of Glycogen Storage Disease Type II by an Adeno-associated Virus Vector Containing a Muscle-Specific Promoter. *Molecular Therapy*. vol. 11, No. 6 pp. 889-898 (2005).
Sun et al., Efficacy of an Adeno-associated Virus 8-Pseudotyped Vector in Glycogen Storage Disease Type II. *Molecular Therapy*. vol. 11, No. 1 pp. 57-65 (2005).
Maxwell et al., "An adenovirus type 5 mutant with the preterminal protein gene deleted efficiently provides helper functions for the production of recombinant adeno-associated virus," Journal of Virology, vol. 72, No. 10, pp. 8371-8373 (1998).
Shayakhmetov et al., "A High-Capacity, Capsid-Modified Hybrid Adenovirus/Adeno-Associated Virus Vector for Stable Transduction of Human Hematopoietic Cells," Journal of Virology, vol. 76, No. 3, pp. 1135-1143 (2002).
Zhang and Li, "Generation of Recombinant Adeno-associated Virus Vectors by a Complete Adenovirus-Mediated Approach," Mol. Ther. vol. 3, No. 5, Part 1, pp. 787-792 (2001).

* cited by examiner

VIRAL VECTORS AND METHODS FOR PRODUCING AND USING THE SAME

CROSS REFERENCE TO RELATED APPLICATIONS

This application is based on and claims priority to U.S. Provisional Application Ser. No. 60/376,397, filed Apr. 30, 2002, herein incorporated by reference in its entirety.

GRANT STATEMENT

This work was supported by grant R01-DK 52925 from the U.S. National Institute of Health. Thus, the U.S. government has certain rights in the invention.

FIELD OF THE INVENTION

The present invention relates to reagents and methods for producing viral vectors, in particular stocks of adeno-associated virus (AAV). The invention further relates to novel viral vectors and methods of administering the same in vitro and in vivo.

BACKGROUND OF THE INVENTION

Limitations of AAV vectors include inefficient production methods, packaging size constraints (introduced gene no larger than 4.5 kb), and a high level of immunity to AAV among adults (although AAV infection is not associated with any disease). The first AAV vectors were produced by transfection of 293 cells with two plasmids (an AAV vector plasmid and an AAV helper plasmid), and infection with adenovirus (reviewed in Muzyczka, (1992) *Curr. Topics Microbiol. Immunol.* 158:97-129). This method provided the essential elements needed for AAV vector production, including AAV terminal repeat (TR) sequences flanking a gene of interest, AAV helper functions consisting of the rep and cap genes, and adenovirus genes.

Improvements to the basic method have included: delivery of adenovirus genes by transfection to eliminate contaminating adenovirus (Grimm et al. (1998) *Hum. Gene Ther.* 9:2745-2760, Matsushita et al. (1998) *Gene Ther.* 5:938-945, Xiao et al. (1998) *J. Virol.* 72:10222-10226); delivery of AAV vector sequences within an Ad/AAV hybrid vector to increase vector production (Gao et al. (1998) *Gene Ther.* 9:2353-2362, Liu et al. (1999) *Gene Ther.* 6:293-299); and construction of first generation packaging cell lines containing the AAV rep and cap genes (Clark et al. (1995) *Hum. Gene Ther.* 6:1329-1341, Gao et al. (1998) *Gene Ther.* 9:2353-2362, Inoue & Russell (1998) *J. Virol.* 72:7024-7031, Liu et al. (1999) *Gene Ther.* 6:293-299, Tamayose et al. (1996) *Hum. Gene Ther.* 7:507-513, Yang et al. (1994) *J. Virol.* 68:4847-4856).

Glycogen storage disease type II (GSD II) presents as a classical lysosomal storage disorder, characterized by lysosomal accumulation of glycogen and tissue damage, primarily in muscle and heart (Hirschhorn et al. (2001) Glycogen Storage Disease Type II: Acid α-Glucosidase (Acid Maltase) Deficiency, p. 3389-3419. In C. R. Scriver, A. L. Beaudet, W. S. Sly, and D. Valle (eds.), *The Metabolic and Molecular Basis for Inherited Disease*. McGraw-Hill, N.Y.). Administration of a modified adenovirus vector encoding murine GAA or hGAA that was targeted to mouse liver reversed the glycogen accumulation in a GAA-knockout (GAA-KO) mouse model for Pompe disease within days, although the effect diminished with time (Amalfitano et al. (1999) *Proc. Natl. Acad. Sci. U.S.A.* 96:8861-8866, Ding et al. (2001) *Hum. Gene Ther.* 12:955-965, Pauly et al. (2001) *Human Gene Ther.* 12:527-538). AAV vectors have reversed the abnormalities in mouse models for hemophilia B (Snyder et al. (1999) *Nat. Med.* 5:64-70 [see comments]), Sly disease (Daly et al. (1999) *Proc. Natl. Acad. Sci. U.S.A.* 96:2296-2300), and for Fabry disease (Jung et al. (2001) *Proc. Natl. Acad. Sci. U.S.A.* 98:2676-2681) with long-term benefits, but not yet for GSD II.

In accordance with the present invention, highly increased AAV vector packaging with a hybrid Ad-AAV vector has been observed, and a modified adenovirus has been utilized, such that no contaminating Ad particles are produced during AAV packaging. Both the Ad and AAV versions of the vector encoding hGAA have been administered to the GAA-KO mouse model for GSD II. The hybrid Ad-AAV vector provides advantages for the development of gene therapy for GSD II, including but not limited to: (a) transgene delivery in vivo; (2) improved packaging of an AAV vector that delivered human GAA in the GAA-KO mouse; and (3) a combination thereof.

SUMMARY OF INVENTION

One aspect of the present invention is based on an improved method for producing stocks of adeno-associated virus (AAV) using a novel hybrid adenovirus comprising a recombinant AAV vector genome embedded within the adenovirus backbone. Traditional methods of AAV production are known to have a number of drawbacks, including, low yield, contamination with adenovirus particles, and reliance on E1a+ packaging cell lines (e.g., 293 cells). The novel hybrid adenovirus comprises an adenovirus backbone that does not express a functional polymerase and/or preterminal protein (pTP), for example, by deletion within these regions. The resulting virus is replication-incompetent and cannot complete viral replication or produce new virus particles. The hybrid adenovirus may contain deletions in regions other than the polymerase or pTP regions. Moreover, the hybrid adenovirus may be E1 a+ or E1a−.

Use of the inventive reagents and methods may improve AAV production titers, reduce or even essentially eliminate contamination with adenovirus, and allow for the use of an E1a+ hybrid adenovirus (or an additional E1a+ adenovirus), thereby decreasing reliance on an E1a+ packaging cell. Moreover, improved packaging cell lines expressing the AAV Rep proteins (and, optionally, capsid protein) may be possible if the E1 a genes are provided by a vector rather than the cell.

Thus, the present invention provides a recombinant hybrid virus that can be used to prepare an AAV gene therapy vector, including AAV pseudotype vectors. In a representative embodiment of the invention, a recombinant hybrid virus comprises: (a) a deleted adenovirus vector genome comprising the adenovirus 5' and 3' cis-elements for viral replication and encapsidation, and further comprising a deletion in an adenovirus genomic region selected from the group consisting of: (i) the polymerase region, wherein said deletion essentially prevents the expression of a functional polymerase protein from said deleted region and said hybrid virus does not otherwise express a functional polymerase protein, (ii) the preterminal protein region, wherein said deletion essentially prevents the expression of a functional preterminal protein from said deleted region, and said hybrid virus does not otherwise express a functional preterminal protein, and (iii) both the regions of (i) and (ii); and (b) a recombinant adeno-associated virus (AAV) vector genome flanked by the adenovirus vector genome sequences of (a), said recombinant AAV vector genome comprising (i) AAV 5' and 3' inverted terminal repeats, (ii) and AAV packaging sequence, and (iii) a heterologous nucleic acid sequence, wherein said heterologous nucleic acid sequence is flanked by the 5' and 3' AAV inverted terminal repeats of (i).

Thus, the invention provides novel AAV vectors for delivery of a heterologous nucleic acid sequence of interest (e.g., GAA) to a target cell (e.g., a skeletal muscle, smooth muscle, cardiac muscle or diaphragm cell) in vitro or in vivo. In particular embodiments, the novel rAAV vector is a rAAV1, rAAV5, rAAV6 vector comprising a heterologous nucleic acid sequence encoding GAA. In other embodiments, the novel rAAV vector is a pseudotyped vector comprising a capsid from one AAV serotype (e.g., AAV1, AAV5, or AAV6); ITRs from another serotype (e.g., AAV2 ITRs); and/or a heterologous nucleic acid sequence encoding GAA. The vector may be delivered to a desired target cell in vitro or in vivo (e.g., a skeletal muscle, cardiac muscle, smooth muscle or diaphragm cell). In preferred embodiments, the invention provides a rAAV6 or pseudotyped rAAV6 (e.g., with AAV2 terminal repeat sequences) vector comprising a heterologous nucleic acid sequence encoding a polypeptide or antisense sequence of interest for delivery to skeletal, cardiac or diaphragm muscle (e.g., a nucleic acid sequence encoding GAA, dystrophin, or a sarcoglycan).

A recombinant hybrid virus of the invention can also be used directly for gene therapy applications. Thus, the present invention provides a method for delivering a nucleic acid sequence to a cell (in vitro or in vivo) using the inventive hybrid adenovirus particles comprising a recombinant AAV vector genome. Typically, the recombinant AAV (rAAV) vector genome will comprise the 5' and 3' AAV inverted terminal repeat (ITR) sequences flanking the transgene of interested. In turn, the rAAV genome is inserted into the inventive adenovirus backbone (e.g., in the E1 a region) to produce the hybrid virus. Gene delivery using the hybrid adenovirus may advantageously combine benefits associated with both AAV (e.g., possibility for site-specific integration, persistent expression) and adenovirus (e.g., large carrying capacity for transgenes, high level infection of target cells). The method may be carried out to deliver any transgene of interest. Methods of treating subjects with lysosomal acid α-glycosidase (GAA) deficiency are of particular interest.

Accordingly, it is an object of the present invention to provide a recombinant hybrid virus, and methods for preparing the same. The recombinant hybrid virus is useful for therapeutic applications and for large scale AAV production, among other applications. This and other objects are achieved in whole or in part by the present invention.

An object of the invention having been stated above, other objects and advantages of the present invention will become apparent to those skilled in the art after a study of the following description of the invention and non-limiting Examples.

BRIEF DESCRIPTION OF THE DRAWINGS

FIG. 5A depicts Western blot analysis of plasma from GAAKO\SCID mice at the indicated times following portal vein injection of the indicatedAAV vector encoding hGAA, and from untreated, GAA-KO\SCID mice (Controls). Each lane represents an individual mouse.

FIG. 5B is a bar graph that summarizes GAA analysis for tissues following portal vein injection of an AAV vector. GAA-KO/SCID mice received the vector packaged as AAV2 (n=1) or AAV6 (n=1). Controls were age-matched, untreated GAA-KO/SCID mice (n=2). The GM level was analyzed twice, independently, and the average and range are shown.

FIG. 5C is a photomicrograph depicting periodic acid Schiff (PAS) staining of the heart for a GAA-KO/SCID mouse that received an AAV vector (left panel—AAV-CB-GAApA) and for an untreated GAA-KO/SCID mouse (right panel) and HE staining (lower panels). Magnification 100×.

DETAILED DESCRIPTION OF THE INVENTION

Figure 1A:
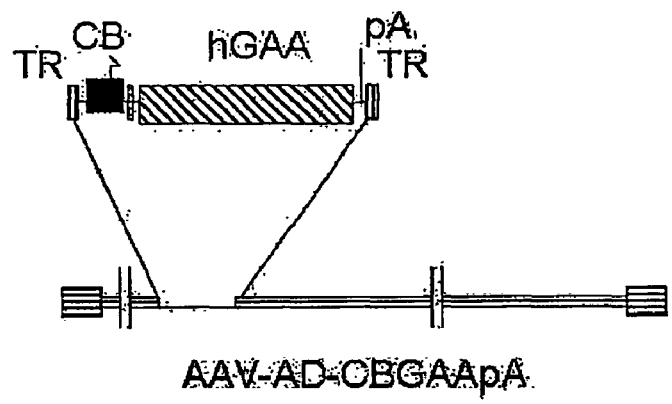
FIG. 1A is a schematic of a hybrid Ad-AAV vector containing the chicken beta-actin (CB) promoter driving the hGAA cDNA. The hybrid vector, AdAAVCBGAApA, was constructed by bacterial recombination. The packaging size for the AAV vector sequence is 4.4 kb.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure that do not depart from the instant invention. Hence, the following specification is intended to illustrate some particular embodiments of the invention, and not to exhaustively specify all permutations, combinations and variations thereof.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The references cited in the specification are incorporated herein by reference to the extent that they supplement, explain, provide a background for or teach methodology, techniques and/or compositions employed herein.

The following U.S. patents are herein incorporated by reference in their entirety: U.S. Pat. Nos. 6,328,958; 6,258,595; 6,294,370; 5,872,005; 6,270,996; 6,329,181; 6,251,677; 5,871,982; and 6,156,303.

I. Definitions

While the following terms are believed to be well understood by one of ordinary skill in the art, the following definitions are set forth to facilitate explanation of the invention. The terminology used in the description of the invention herein is for the purpose of describing particular embodiments only and is not intended to be limiting of the invention.

The term "adenovirus" as used herein is intended to encompass all adenoviruses, including the Mastadenovirus and Aviadenovirus genera. To date, at least forty-seven human serotypes of adenoviruses have been identified (see, e.g., FIELDS et al., VIROLOGY, volume 2, chapter 67 (3d ed., Lippincott-Raven Publishers). Preferably, the adenovirus is a serogroup C adenovirus, still more preferably the adenovirus is serotype 2 (Ad2) or serotype 5 (Ad5).

Except as otherwise indicated, standard methods may be used for the construction of the recombinant adenovirus genomes, helper adenoviruses, and packaging cells according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

Those skilled in the art will appreciate that the inventive adenovirus vectors may be modified or "targeted" as described in Douglas et al., (1996) *Nature Biotechnology* 14:1574; U.S. Pat. No. 5,922,315 to Roy et al.; U.S. Pat. No. 5,770,442 to Wickham et al.; and/or U.S. Pat. No. 5,712,136 to Wickham et al. (the disclosures of which are all incorporated herein in their entirety).

As used herein, the term "vector" or "gene delivery vector" may refer to an Ad particle that functions as a gene delivery vehicle, and which comprises vDNA (i.e., the vector genome) packaged within an Ad capsid. Alternatively, in some contexts, the term "vector" may be used to refer to the vector genome/vDNA.

An "Ad vector genome" refers to the viral genomic DNA, in either its naturally occurring or modified form. Thus, the term "Ad vector genome" also refers to nucleic acids derived from an Ad genome. A "rAd vector genome" is a recombinant Ad genome (i.e., VDNA) that comprises one or more heterologous nucleotide sequence(s). The Ad vector genome or rAd vector genome will typically comprise the Ad terminal repeat sequences and packaging signal. An "Ad particle" or "rAd particle" comprises an Ad vector genome or rAd vector genome, respectively, packaged within an Ad capsid. Generally, the Ad vector genome is most stable at sizes of about 28 kb to 38 kb. (approximately 75% to 105% of the native genome size). In the case of an adenovirus vector containing large deletions and a relatively small transgene, "stuffer DNA" can be used to maintain the total size of the vector within the desired range by methods known in the art.

By "infectious", as used herein, it is meant that the adenovirus can enter the cell by natural transduction mechanisms and express the transgene therein. Alternatively, an "infectious" adenovirus is one that can enter the cell by other mechanisms and express the transgene therein. As one illustrative example, the vector can enter a target cell by expressing a ligand or binding protein for a cell-surface receptor in the adenovirus capsid or by using an antibody(ies) directed against molecules on the cell-surface followed by internalization of the complex, as is described hereinbelow.

The term "replication" or "Ad replication" as used herein, refers specifically to replication (i.e., making new copies of) of the Ad vector genome (i.e., virion DNA).

The term "propagation" as used herein refers to a productive viral infection wherein the viral genome is replicated and packaged to produce new virions, which typically can "spread" by infection of cells beyond the initially infected cell. A "propagation-defective" virus is impaired in its ability to produce a productive viral infection and spread beyond the initially infected cell.

The terms "nucleic acid molecule" or "nucleic acid" each refer to deoxyribonucleotides or ribonucleotides and polymers thereof in single-stranded, double-stranded, or triplexed form. Unless specifically limited, the term encompasses nucleic acids containing known analogues of natural nucleotides that have similar properties as the reference natural nucleic acid. The terms "nucleic acid molecule" or "nucleic acid" can also be used in place of "gene", "cDNA", or "mRNA". Nucleic acids can be synthesized, or can be derived from any biological source, including any organism.

The term "heterologous nucleic acids" refers to a sequence that originates from a source foreign to an intended host cell or, if from the same source, is modified from its original form. Thus, a heterologous nucleic acid in a host cell includes a gene that is endogenous to the particular host cell, but which has been modified, for example by mutagenesis or by isolation from native cis-regulatory sequences. The term "heterologous nucleic acid" also includes non-naturally occurring multiple copies of a native nucleotide sequence. The term "heterologous nucleic acid" also encompasses a nucleic acid that is incorporated into a host cell's nucleic acids, however at a position wherein such nucleic acids are not ordinarily found. The term "transgene" is also used herein interchangeably with the term "heterologous nucleic acid."

The term "recombinant" generally refers to an isolated nucleic acid that is replicable in a non-native environment. Thus, a recombinant nucleic acid can comprise a non-replicable nucleic acid in combination with additional nucleic acids, for example vector nucleic acids, which enable its replication in a host cell. The term "recombinant" is also used to describe a vector (e.g., an adenovirus or an adeno-associated virus) comprising recombinant nucleic acids.

The term "gene" refers broadly to any segment of DNA associated with a biological function. A gene can comprise sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "operatively linked", as used herein, refers to a functional combination between a promoter region and a nucleic acid molecule such that the transcription of the nucleic acid molecule is controlled and regulated by the promoter region. Techniques for operatively, linking a promoter region to a nucleic acid molecule are known in the art.

The term "vector" is used herein to refer to a nucleic acid molecule having nucleotide sequences that enable its replication in a host cell. A vector can also include nucleic acids to permit ligation of nucleotide sequences within the vector, wherein such nucleic acids are also replicated in a host cell. Representative vectors include plasmids, cosmids, and viral vectors. The term "vector" is also used to describe an expression construct, wherein the expression construct comprises a vector and a nucleic acid operatively inserted with the vector, such that the nucleic acid is expressed.

Vectors can also comprise nucleic acids including expression control elements, such as transcription/translation control signals, origins of replication, polyadenylation signals, internal ribosome entry sites, promoters, enhancers, etc., wherein the control elements are operatively associated with a nucleic acid encoding a gene product. Selection of these and other common vector elements are conventional and many such sequences can be derived from commercially available vectors. See e.g., Sambrook et al. (1989) *Molecular Cloning: A Laboratory Manual*. Cold Spring Harbor Laboratory Press, Cold Spring Harbor, and references cited therein.

The terms "cis-acting regulatory sequence" or "cis-regulatory motif" or "response element", as used herein, each refer to a nucleotide sequence within a promoter region that enables responsiveness to a regulatory transcription factor. Responsiveness can encompass a decrease or an increase in transcriptional output and is mediated by binding of the transcription factor to the DNA molecule comprising the response element.

The term "transcription factor" generally refers to a protein that modulates gene expression by interaction with the cis-regulatory element and cellular components for transcription, including RNA Polymerase, Transcription Associated Factors (TAFs), chromatin-remodeling proteins, reverse tet-responsive transcriptional activator, and any other relevant protein that impacts gene transcription.

The term "promoter" defines a region within a gene that is positioned 5' to a coding region of a same gene and functions to direct transcription of the coding region. The promoter region includes a transcriptional start site and at least one cis-regulatory element. The term "promoter" also includes functional portions of a promoter region, wherein the functional portion is sufficient for gene transcription. To determine nucleotide sequences that are functional, the expression of a reporter gene is assayed when variably placed under the direction of a promoter region fragment.

Promoter region fragments can be conveniently made by enzymatic digestion of a larger fragment using restriction endonucleases or DNAse I. Preferably, a functional promoter region fragment comprises about 5000 nucleotides, more preferably 2000 nucleotides, more preferably about 1000 nucleotides. Even more preferably a functional promoter region fragment comprises about 500 nucleotides, even more preferably a functional promoter region fragment comprises about 100 nucleotides, and even more preferably a functional promoter region fragment comprises about 20 nucleotides.

The term "about", as used herein when referring to a measurable value such as an amount of virus (e.g., titer), dose (e.g. an amount of a chemical inducer), time, temperature (e.g., a temperature for induction of a heat-inducible promoter), etc., is meant to encompass variations of ±20% or ±10%, more preferably ±5%, even more preferably ±1%, and still more preferably ±0.1% from the specified amount, as such variations are appropriate to perform the disclosed method.

As used in the description of the invention and the appended claims, the singular forms "a", "an" and "the" are intended to include the plural forms as well, unless the context clearly indicates otherwise.

II. Hybrid Vectors

In a preferred embodiment, a hybrid vector in accordance with the present invention comprises a deleted adenovirus vector genome comprising the adenovirus 5' and 3' cis-elements for viral replication and encapsidation, and further comprising a deletion in an adenovirus genomic region selected from the group consisting of: (i) the polymerase region, wherein said deletion essentially prevents the expression of a functional polymerase protein from said deleted region and said hybrid virus does not otherwise express a functional polymerase protein, (ii) the preterminal protein region, wherein said deletion essentially prevents the expression of a functional preterminal protein from said deleted region, and said hybrid virus does not otherwise express a functional preterminal protein, and (iii) both the regions of (i) and (ii).

Continuing with a preferred embodiment, a hybrid vector of the present invention further comprises a recombinant adeno-associated virus (AAV) vector genome flanked by the adenovirus vector genome sequences disclosed above. The recombinant AAV vector genome comprise (i) AAV 5' and 3' inverted terminal repeats, (ii) an AAV packaging sequence, and (iii) a heterologous nucleic acid sequence, wherein the heterologous nucleic acid sequence is flanked by the 5' and 3' AAV inverted terminal repeats of (i).

A hybrid virus particle comprising a recombinant hybrid virus of the present invention is also provided. The hybrid virus particle is encapsidated within an adenovirus capsid. A cell comprising the recombinant hybrid virus or the hybrid virus particle of the present invention is also provided.

II.A. Deleted Adenovirus Vectors

As noted above, a deleted adenovirus vector genome of the present invention preferably comprises the adenovirus 5' and 3' cis-elements for viral replication and encapsidation, and further comprises a deletion in an adenovirus genomic region selected from the group consisting of: (i) the polymerase region, wherein the deletion essentially prevents the expression of a functional polymerase protein from the deleted region and the hybrid virus does not otherwise express a functional polymerase protein, (ii) the preterminal protein region, wherein the deletion essentially prevents the expression of a functional preterminal protein from the deleted region, and the hybrid virus does not otherwise express a functional preterminal protein, and (iii) both the regions of (i) and (ii).

Optionally, the adenovirus 5' and 3' cis-elements comprise 5' and 3' adenovirus inverted terminal repeats and an adenovirus packaging sequence. In this case, the adenovirus packaging sequence can further comprise the E1A enhancer, which is embedded in the packaging signal.

The adenovirus vectors of the invention have an impairment in polymerase (pol) activity, preterminal protein region (pTP) activity, or a combination thereof (e.g., produced reduced levels of functional pol protein and/or functional pTP protein). Preferably, the Ad vector produces essentially no detectable pol or pTP activity. The [pol–], [rTP–], and [pol–, pTP–] adenoviral vectors of the invention are replication competent, but impaired in their ability to propagate (as defined above). Stated another way, a deleted Ad vector of the present invention is impaired in its ability to package new virions in the absence of transcomplementation, which is provded, for example, by a packaging cell that expresses the Ad pol protein, by a packaging cell that expresses the Ad pTP protein, or by a packaging cell that expresses both the Ad pol protein and the Ad pTP protein.

A [pol–] Ad of the invention preferably has essentially no detectable pol activity (alternatively, essentially no detectable pol transcript or protein). Alternatively, in other embodiments, pol activity (alternatively, pol transcripts or protein) can be reduced by about 70%, 80%, 90%, 95%, 98%, 99% or more as compared with wild-type Ad or [pol+] Ad.

A [pTP–] Ad of the invention preferably has essentially no detectable pTP activity (alternatively, essentially no detectable pTP transcript or protein). Alternatively, in other embodiments, pTP activity (alternatively, pTP transcripts or protein) can be reduced by about 70%, 80%, 90%, 95%, 98%, 99% or more as compared with wild-type Ad or [pTP+] Ad.

A [pol–, pTP–] Ad of the invention preferably has essentially no detectable pol activity and have essentially no detectable pTP activity (alternatively, essentially no detectable pol transcript or protein and essentially no detectable pTP transcript or protein). Alternatively, in other embodiments, pol and pTP activity (alternatively, pol transcripts or protein and pTP transcripts or protein) can be reduced by about 70%, 80%, 90%, 95%, 98%, 99% or more as compared with wild-type Ad or [pol+, pTP+] Ad.

Alternatively stated, a propagation-defective Ad of the invention is impaired in their ability to produce a productive infection in the absence of transcomplementation. Preferably, essentially no new virions are detected following infection with the inventive [pol−], [rTP−], and [pol−, pTP−] adenoviral vectors. Alternatively, production of new virions in infected cells may be reduced by at least about 50%, 60%, 70%, 80%, 90%, 95%, 98%, 99% or more as compared with a wild-type Ad infection or, alternatively, as compared with new virion production in a cell line that can transcomplement the loss of pol function and/or the loss of pTP function.

The Ad genome can be modified by any mutation known in the art (e.g., an insertion, missense, nonsense and/or deletion mutation), so as to result in an impairment in pol activity expressed by the Ad genome and/or so as to produce an impairment in pTP activity expressed in the Ad genome. Preferably, the mutation or alteration to the pol coding region is a deletion mutation, more preferably a deletion mutation that essentially ablates (e.g., essentially eliminates) pol activity. Preferably, the mutation in the pol and/or pTP coding regions are not temperature-sensitive mutations.

The term "deleted vector," as used herein to describe a type of Ad, refers to an Ad wherein one or more, but not all Ad genes have been deleted. Thus, the [pol−], [rTP−], and [pol−, pTP−] adenoviral vectors of the invention specifically exclude "gutted" adenoviral vectors (as that term is understood in the art, see e.g., Lieber, et al., (1996) *J. Virol.* 70:8944-60) in which essentially all of the adenovirus genomic sequences are deleted.

Thus, in preferred embodiments, the vector genome packaged within [pol−] particle has one or more deletions in the pol coding region. Similarly, a vector genome packaged within a [pTP−] particle has one or more deletions in the pTP coding region. The deletion(s) preferably prevents, or essentially prevents, the expression of a functional form of a pol protein and/or a pTP protein from the deleted region.

The term "produces essentially no functional protein," as used herein, means that essentially no pol and/or pTP protein or activity is detectable (e.g., at most, only an insignificant amount is detectable) following infection of non-complementing cells with the inventive [pol−], [pTP−], and [pol−, pTP−] adenoviral vectors. The defect resulting in essentially no functional protein can be at the level of transcription, translation and/or post-translational processes. Thus, even if there is transcription and translation of the pol and/or pTP gene, the resulting protein has essentially no detectable biological activity. Pol and pTP activities can be evaluated by any method known in the art.

As used herein, a "functional" protein is one that retains at least one biological activity normally associated with that protein. Preferably, a "functional" protein retains all of the activities possessed by the unmodified protein. A "non-functional" protein is one that exhibits essentially no detectable biological activity normally associated with the protein (e.g., at most, only an insignificant amount).

The term "deleted" as used herein refers to the omission of at least one nucleotide from the relevant coding region of the adenovirus genome. Deletions can be greater than about 1, 2, 3, 5, 7, 10, 15, 20, 50, 75, 100, 150, 200, or even 500 nucleotides, or more. Deletions in the relevant coding region of the adenovirus genome can be at least about 1%, 5%, 10%, 25%, 50%, 75%, 85%, 90%, 95%, 99%, or more of the coding region. Alternately, the entire coding region of interest (e.g., the entire pol coding region and/or the entire pTP coding region) of the adenovirus genome is deleted. Preferably, the deletion prevents or essentially prevents the expression of a functional protein from the coding region.

In a preferred embodiment of the invention, a deletion comprises a pol region including about nucleotide 7274 to about nucleotide 7881 of an adenovirus serotype 5 genome. Those skilled in the art will appreciate that similar deletions can be made in the homologous regions of the adenovirus genomes from other serotypes.

In another preferred embodiment of the invention, a deletion comprises a pTP region including about nucleotide 9198 to about nucleotide 9630 of an adenovirus serotype 5 genome. Those skilled in the art will appreciate that similar deletions can be made in the homologous regions of the adenovirus genomes from other serotypes.

The various regions of the adenovirus genome have been mapped and are understood by those skilled in the art (see, e.g., FIELDS et al., VIROLOGY, volume 2, chapters 67 and 68 (3d ed., Lippincott-Raven Publishers). The genomic sequences of the various Ad serotypes, as well as the nucleotide sequence of the particular coding regions of the Ad genome, are known in the art and may be accessed, e.g., from GenBank.

In general, larger deletions are preferred as these have the additional advantage that they will increase the capacity of the deleted adenovirus to carry a heterologous nucleotide sequence of interest.

In particular embodiments, [pol−], [ptP−], and [pol−, ptP−] adenoviral vectors of the invention contain mutations or deletions in other regions of the Ad genome. Additional deletions will advantageously increase the carrying capacity of the vector and reduce the likelihood of recombination to generate replication competent virus. Preferably, the additional deletions do not unduly impair the ability of the resulting virus to replicate in desired target cells (e.g., does not reduce replication by more than about 40%, 50%, 60%, 70% or more). For example, the E3 coding region can be deleted, without the provision of E3 by transcomplementation.

In one embodiment, the adenovirus vector genome further comprises a deletion in an adenovirus E1 region. In this case, the deletion preferably essentially prevents the expression of one or more functional E1 proteins from the deleted region. More preferably, the adenovirus vector genome does not otherwise express a functional E1 gene product. Optionally, a recombinant AAV genome as disclosed herein is inserted into the deleted adenovirus E1 region of the adenovirus vector genome.

Additionally, the adenovirus vector genome can further comprise a deletion in an adenovirus region selected from the group consisting of the IVa2 region, the 100K region, the E2a region, the E4 region, the L1 region, the L2 region, the L3 region, the L4 region, the L5 region, the intermediate gene IX region, and any combination of the foregoing. In this case it is preferred that the adenovirus vector genome does not otherwise express a gene product associated with the deleted region. By way of particular example, open reading frames (orf's) 1-5 of the E4 region can be deleted.

It should be noted that the E2a region and the E4orf6 region facilitate high level AAV production. Thus, if these regions are deleted, it is preferred that these regions be provided elsewhere, e.g., by a second Ad, by a packaging cell, or by a plasmid. Also, preferably, the deletion(s) in the Ad genome are selected so as not to interfere with other Ad functions essential for viral replication in target cells of interest.

The inventive deleted adenoviruses are impaired in their ability to propagate (i.e., produce new virions) without complementation to compensate for the loss of pol and/or pTP function, e.g., by a packaging cell. As described in more detail hereinbelow, the packaging cell will typically be stably modified to express a functional pol and/or pTP protein. In the presence of transcomplementing functions, the [pol−],

[pTP−], and [pol−, pTP−] adenoviral vectors of the invention can replicate and package new virions.

The adenovirus vector genome can further comprise nucleic acids encoding an AAV capsid protein. The adenovirus vector genome can also comprise nucleic acids encoding an AAV Rep protein. In this case, the sequences encoding the AAV Rep protein can be operably associated with an inducible promoter. The inducible promoter can be selected from a group including but not limited to a tetracycline response element, an ecdysone response element, a heat shock promoter, an MMLV long terminal repeat sequence, a bacteria phage T7 promoter, a metalothionein response element, and an AAV p5 promoter. Alternatively, the sequences encoding said AAV Rep protein are operably associated with a tissue-specific promoter selected from a group including but not limited to a liver-specific, muscle-specific, and brain-specific promoter.

The adenovirus vector genome can optionally comprise nucleic acids encoding the adenovirus helper functions for AAV replication and packaging. In this case, the adenovirus vector genome preferably comprises a functional adenovirus genomic region selected from the group consisting of an adenovirus E1 a region, E2a region, E4orf6 region, VA RNA region, and any combination of the foregoing.

II.B. Recombinant Adeno-Associated Virus Vector Genome

In a preferred embodiment a hybrid vector in accordance with the present invention further comprises a recombinant adeno-associated virus (AAV) vector genome flanked by the adenovirus vector genome sequences disclosed herein above. The recombinant AAV vector genome preferably comprises: (i) AAV 5' and 3' inverted terminal repeats, (ii) an AAV packaging sequence, and (iii) a heterologous nucleic acid sequence, wherein the heterologous nucleic acid sequence is flanked by the 5' and 3' AAV inverted terminal repeats of (i).

More preferably, the AAV inverted terminal repeats are selected from the group consisting of AAV-1, AAV-2, AAV-3, AAV-4, AAV-5 and AAV-6 inverted terminal repeats. Optionally, the AAV vector genome does not encode the AAV Rep or AAV capsid proteins.

II.C. Heterologous Nucleotide Sequences

As described in more detail hereinbelow, any of the inventive hybrid viruses described above can further comprise one or more heterologous nucleotide sequences (e.g., two, three, four, five, six or more sequences) of interest. For example, in one embodiment, the heterologous nucleic acid sequence encodes an antisense nucleic acid sequence.

In another embodiment the heterologous nucleic acid sequence is operatively associated with an expression control sequence. A representative expression control sequence comprises a promoter. Representative promoters include but are not limited to a liver-specific, muscle-specific, brain-specific promoter and a glucose-responseive promoter. A preferred liver-specific promoter is the alpha1 anti-trypsin promoter. A preferred glucose-responsive promoter is the canine glucose-6-phosphatase promoter. (Kishnani et al. (2001) *Vet Path.* 38:83-91). Optionally, the promoter is an inducible promoter. Other representative promoters include but are not limited to the CMV promoter, albumin promoter, EF1-α promoter, PγK promoter, MFG promoter, and Rous sarcoma virus promoter.

In another embodiment the heterologous nucleic acid sequence encodes a polypeptide. Representative polypeptides include but are not limited to a therapeutic polypeptide, an immunogenic polypeptide, and a reporter polypeptide. Particular examples of such polypeptides are set forth herein below.

III. Methods for Making Viral Vectors

Methods for making viral vectors are also provided in accordance with the present invention. In a preferred embodiment, a method of producing a recombinant adeno-associated virus (AAV) particle is provided. The method comprises providing to a cell: (a) a recombinant hybrid virus according to o the present invention or a hybrid virus particle comprising a recombinant hybrid virus encapsidated with an adenovirus capsid; (b) AAV sequences sufficient for replication and packaging of the AAV vector genome; (c) AAV sequences sufficient to produce a functional AAV capsid, wherein (a), (b) and (c) are provided to the cell under conditions sufficient for replication of the AAV vector genome and packaging thereof in the AAV capsid such that AAV particles comprising the AAV vector genome encapsidated within the AAV capsid are produced in the cell. Representative cells include but are not limited to a HeLa cell, a 293 cell, a muscle cell, and a liver cell. The recombinant AAV particle can be collected in any desired manner. In a preferred embodiment recombinant AAV particles are collected by column purification.

Optionally, the method further comprises providing to the cell the adenovirus helper functions for AAV replication and packaging. Representative sequences that provide adenovirus helper functions include but are not limited to adenovirus E1a, E2a, E4orf6, and VA RNA helper sequences.

In one embodiment, the cell stably expresses sequences encoding an AAV Rep protein and/or sequences encoding the AAV capsid protein. The term "stable", as used herein with respect to gene expression, is meant to refer to and encompass inducible and/or constitutive expression. In another embodiment, a vector other than the recombinant hybrid virus provides sequences encoding an AAV Rep protein and/or sequences encoding the AAV capsid protein. Represesntative such vectors include but are not limted to a plasmid, an adenovirus, an Epstein Barr virus, and a herpesvirus vector.

Optionally, the AAV inverted terminal repeats and the AAV capsid are derived from different AAV serotypes. In one embodiment, the AAV inverted terminal repeats are AAV-2 inverted terminal repeats. In another embodiment, the AAV capsid is an AAV-6 capsid. In yet another embodiment, the AAV inverted terminal repeats are AAV-2 inverted terminal repeats and the AAV capsid is an AAV-6 capsid. The term AAV-6 capsid refers to an AAV6 capsid comprising one or more AAV6 capsid proteins.

Preferably, essentially no adenovirus particles are produced when AAV are prepared using a deleted Ad or the present invention. Also preferably, the yield of recombinant AAV particles is at least 5-fold greater than AAV pepared using a pol+ and/or a pTP+Ad.

A method of producing a recombinant adeno-associated virus (AAV) particle is also provided. The method comprises providing to a cell a hybrid virus particle according to the present invention, the recombinant hybrid virus particle expressing the adenovirus helper functions for AAV replication and packaging; wherein the cell (i) expresses AAV rep sequences sufficient for replication and packaging of the AAV vector genome, (ii) expresses AAV cap sequences sufficient to produce a functional AAV capsid, and (iii) does not express sequences sufficient to produce a functional adenovirus E1a protein; and further wherein the hybrid virus particle is provided under conditions sufficient for replication of the AAV vector genome and packaging thereof in the AAV capsid such that AAV particles comprising the AAV vector genome encapsidated within the AAV capsid are produced in the cell.

In another embodiment, the method of producing a recombinant adeno-associated virus (AAV) particle comprises providing to a cell a hybrid virus particle according to the present invention. In this embodiment, the hybrid virus particle expresses: (i) adenovirus helper functions for AAV replication and packaging except the hybrid virus particle does not express a functional adenovirus E1a gene product, (ii) AAV rep sequences sufficient for replication and packaging of the AAV vector genome, and (iii) AAV cap sequences sufficient to produce a functional AAV capsid. The cell expresses functional adenovirus E1a gene products; and the hybrid virus particle is provided to the cell under conditions sufficient for replication of the AAV vector genome and packaging thereof in the AAV capsid such that AAV particles comprising the AAV vector genome encapsidated within the AAV capsid are produced in the cell.

In yet another embodiment, the method of producing a recombinant adeno-associated virus (AAV) particle comprises providing to a cell: (a) a hybrid virus particle according to the present invention; and (b) a separate vector comprising inducible AAV rep sequences sufficient for replication and packaging of the AAV vector genome, and AAV cap sequences sufficient to produce a functional AAV capsid. In this embodiment, the hybrid virus particle expresses adenovirus helper functions for AAV replication and packaging except the hybrid virus particle does not express a functional adenovirus E1a gene product. The cell expresses a functional adenovirus E1a gene product; and the hybrid virus particle and separate vector are provided to the cell under conditions sufficient for replication of the AAV vector genome and packaging thereof in the AAV capsid such that AAV particles comprising the AAV vector genome encapsidated within the AAV capsid are produced in the cell.

In yet a further embodiment, a method of producing a recombinant adeno-associated virus (AAV) particle, comprising providing to a cell: (a) a hybrid virus particle according to the present invention; and (b) a separate vector comprising AAV rep sequences sufficient for replication and packaging of the AAV vector genome, and AAV cap sequences sufficient to produce a functional AAV capsid. The hybrid virus particle expresses adenovirus helper functions for AAV replication and packaging. The cell does not express a functional adenovirus E1a gene product; and the hybric virus particle and the separate vector are provided to the cell under conditions sufficient for replication of the AAV vector genome and packaging thereof in the AAV capsid such that AAV particles comprising the AAV vector genome encapsidated within the AAV capsid are produced in the cell.

In each of the two immediately preceeding embodiments the separate vector is preferably one of a plasmid vector and an adenovirus vector.

IV. Methods for Using Viral Vectors

The present invention provides methods that employ the viral vectors disclosed herein, including hybrid Ad vectors and AAV vectors, in particular AAV6 vectors.

As used herein, a "viral vector" is a virus that carries one or more heterologous nucleotide sequences (i.e., transgenes), e.g., two, three, four, five or more heterologous nucleotide sequences. The viral vectors of the present invention are useful for the delivery of nucleic acids to cells in vitro, ex vivo, and in vivo. In particular, the inventive vectors can be advantageously employed to deliver or transfer nucleic acids to animal cells, more preferably to mammalian cells. Preferably, the sequence is expressed in the cell. Nucleic acids of interest include nucleic acids encoding polypeptides, preferably therapeutic (e.g., for medical or veterinary uses) or immunogenic (e.g., for vaccines) polypeptides. In one embodiment, site-specific integration into human chromosome 19 in cells or in vivo can be accomplished by providing AAV Rep 68/78 protein (or sequences encoding the same) along with a hybrid vector of the present invention.

Alternatively, in particular embodiments of the invention, the nucleic acid of interest may encode therapeutic nucleic acids such as an antisense nucleic acid, a ribozyme, (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) that mediate gene silencing (see, Sharp et al., (2000) *Science* 287:2431) or other non-translated RNAs, such as "guide" RNAs (Gorman et al., (1998) *Proc. Nat Acad. Sci. USA* 95:4929; U.S. Pat. No. 5,869,248), and the like.

As a further alternative, the viral vectors of the present invention can be used to infect a cell in culture to express a desired gene product, e.g., to produce a polypeptide of interest (for example, lysosomal acid α-glucosidase). Preferably, the polypeptide is secreted into the medium and can be purified therefrom using routine techniques known in the art. Signal peptide sequences that direct extracellular secretion of proteins are known in the art and nucleotide sequences encoding the same can be operably linked to the nucleotide sequence encoding the polypeptide of interest by routine techniques known in the art. Alternatively, the cells can be lysed and the expressed recombinant protein can be purified from the cell lysate. The cell can be a bacterial, protozoan, plant, yeast, fungus, or animal cell. Preferably, the cell is an animal cell (e.g., insect, avian or mammalian), more preferably a mammalian cell. Also preferred are cells that are permissive for transduction by viral vectors.

The inventive methods may be used to express any polypeptide of interest, e.g., a therapeutic polypeptide, as described below. Alternatively, the polypeptide can be for use in an industrial process, in particular, an industrial enzyme. Industrial enzymes are known in the art and include, but are not limited to, cellulases, lipases, β-glucanases, hemicellulases, alkaline proteases, α-amylases, xylanases, catalases, lactases, pectinases, isoamylases, amyloglucosidases, invertases, phytases, rennet, and tannases.

Heterologous nucleotide sequences encoding polypeptides also include those encoding reporter polypeptides (e.g., an enzyme). Reporter polypeptides are known in the art and include, but are not limited to, Green Fluorescent Protein, β-galactosidase, alkaline phosphatase, and chloramphenicol acetyltransferase gene.

The present invention also provides vectors useful as vaccines. The antigen can be presented in the adenovirus capsid, alternatively, the antigen can be expressed from a heterologous nucleic acid introduced into a viral vector. Any immunogen of interest can be provided by the viral vector. Immunogens of interest are well-known in the art and include, but are not limited to, immunogens from human immunodeficiency virus (e.g., envelope proteins), influenza virus, gag proteins, cancer antigens, HBV surface antigen (to immunize against hepatitis), rabies glycoproteins, and the like.

An immunogenic polypeptide, or immunogen, can be any polypeptide suitable for protecting the subject against a pathogenic disease, including but not limited to bacterial, protozoal, fungal, and viral diseases. For example, the immunogen can be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products).

The immunogen may also be an arenavirus immunogen (e.g., Lassa virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen can further be a polio immunogen, herpes immunogen (e.g., CMV, EBV, HSV immunogens) mumps immunogen, measles immunogen, rubella immunogen, diptheria toxin or other diptheria immunogen, pertussis immunogen, hepatitis (e.g., hepatitis A or hepatitis B) immunogen, or any other vaccine immunogen known in the art.

Alternatively, the immunogen can be any cancer cell antigen (including tumor cell antigens), or any other antigen that induces an immune response against cancer cells. A "cancer cell antigen," as used herein, is an antigen that is associated cancer in general or with a particular cancer. Preferably, the cancer cell antigen is expressed on the surface of the cancer cell. Exemplary cancer cell antigens are described in S. A. Rosenberg, (1999) *Immunity* 10:281). Other illustrative cancer cell antigens include, but are not limited to: the BRCA1 gene product, BRCA2 gene product, gp100, tyrosinase, GAGE-½, BAGE, RAGE, NY-ESO1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124), MART-1 (Coulie et al., (1991) *J. Exp. Med.* 180: 35), gp100 (Wick et al., (1988) *J. Cutan. Pathol.* 4:201), MAGE antigen, MAGE-1, MAGE-2 and MAGE-3 (Van der Bruggen et al., (1991) *Science,* 254:1643), CEA, TRP-1, TRP-2, P-15, HER-2/neu gene product (U.S. Pat. No. 4,968, 603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623), mucin antigens (international patent publication WO 90/05142), telomerases; nuclear matrix proteins, prostatic acid phosphatase, papilloma virus antigens, and antigens associated with the following cancers: melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others (see, e.g., Rosenberg, (1996) *Ann. Rev. Med.* 47:481-91).

The present invention can be further used to deliver a therapeutic polypeptide. Representatave polypeptides include but are not limited to insulin, myophosphorylase (associated with glycogen storage disease V), VEGF, interleukins, p53, Rb and other anti-cancer proteins.

Other therapeutic polypeptides include, but are not limited to, cystic fibrosis transmembrane regulator protein (CFTR), dystrophin (including the protein product of dystrophin minigenes, see, e.g, Vincent et al., (1993) *Nature Genetics* 5:130), dystrophin-associated polypeptides, sarcoglycans, glycogen phosphorylase, utrophin (Tinsley et al., (1996) *Nature* 384: 349), clotting factors (e.g., Factor XIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, cytokines (e.g., α-interferon, β-interferon, interferon-γ, interleukin-2, interleukin-4, granulocyte-macrophage colony stimulating factor, lymphotoxin, and the like), peptide growth factors and hormones (e.g., somatotropin, insulin, insulin-like growth factors 1 and 2, platelet derived growth factor, epidermal growth factor, fibroblast growth factor, nerve growth factor, neurotrophic factor -3 and -4, brain-derived neurotrophic factor, glial derived growth factor, transforming growth factor -α and -β, and the like), receptors (e.g., the tumor necrosis growth factor receptor), monoclonal antibodies (including single chain monoclonal antibodies). Other illustrative heterologous nucleotide sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), and any other polypeptide that has a therapeutic effect in a subject in need thereof.

In a preferred embodiment of the present invention, the heterologous nucleic acid encodes a polypeptide associated with muscular dystrophy, for example a dystrophan polypeptide, a dystrophin-associated polypeptide, a sarcoglycan polypeptide, and a glycogen phosphorylase polypeptide.

In another preferred embodiment of the invention, the heterologous nucleotide sequence encodes a polypeptide that is associated with a metabolic disorder. By "associated with a metabolic disorder", it is intended that the expressed polypeptide is one that is deficient or defective in a metabolic disorder, or is otherwise a causative agent in a metabolic disorder.

In another preferred embodiment, the polypeptide is a lysosomal polypeptide, more preferably a precursor polypeptide that retains the mannose-6-phosphate residues that are characteristic of proteins targeted to the lysosomal compartment.

In still another preferred embodiment, the heterologous nucleotide sequence encodes a polypeptide that is associated with a lysosomal storage disease. By "associated with a lysosomal storage disease", it is intended that the expressed polypeptide is one that is deficient or defective in a lysosomal storage disorder, or is otherwise a causative agent in a lysosomal storage disorder.

There are a multitude of lysosomal storage diseases, as is recognized in the art. Exemplary lysosomal storage disease include, but are not limited to, GM1 gangliosidosis, Tay-Sachs disease, GM2 gangliosidosis (AB variant), Sandhoff disease, Fabry disease, Gaucher disease, metachromatic leukodystrophy, Krabbe disease, Niemann-Pick disease (Types A-D), Farber disease, Wolman disease, Hurler Syndrome (MPS IH), Scheie Syndrome (MPS IS), Hurler-Scheie Syndrome (MPS IH/S), Hunter Syndrome (MPS II), Sanfilippo A Syndrome (MPS IIIA), Sanfilippo B Syndrome (MPS IIIB), Sanfilippo C Syndrome (MPS IIIC), Sanfilippo D Syndrome (MPS IIID), Morquio A disease (MPS IVA), Morquio B disease (MPS IV B), Maroteaux-Lamy disease (MPS VI), Sly Syndrome (MPS VII), α-mannosidosis, β-mannosidosis, fucosidosis, aspartylglucosaminuria, sialidosis (mucolipidosis I), galactosialidosis (Goldberg Syndrome), Schindler disease, mucolipidosis II (I-Cell disease), mucolipidosis III (pseudo-Hurler polydystrophy), cystinosis, Salla disease, infantile sialic acid storage disease, Batten disease (juvenile neuronal ceroid lipofuscinosis), infantile neuronal ceroid lipofuscinosis, mucolipidosis IV, and prosaposin.

Polypeptides that are associated with lysosomal storage diseases according to the present invention include, but are not limited to, β-galactosidase, β-hexosaminidase A, β-hexosaminidase B, $GM_2$ activator protein, glucocerebrosidase, arylsulfatase A, galactosylceramidase, acid sphingomyelinase, acid ceramidase, acid lipase, α-L-iduronidase, iduronate sulfatase, heparan N-sulfatase, α-N-acetylglucosaminidase acetyl-CoA, glucosaminide acetyltransferase, N-acetylglucosamine-6-sulfatase, arylsulfatase B, β-glucuronidase, α-mannosidase, α-mannosidase, α-L-fucosidase, N-aspartyl-β-glucosaminidase, α-neuraminidase, lysosomal protective protein, α-N-acetyl-galactosaminidase, N-acetyl-glucosamine-1-phosphotransferase, cystine transport protein, sialic acid transport protein, the CLN3 gene product, palmitoyl-protein thioesterase, saposin A, saposin B, saposin C, and saposin D.

The present invention further provides viral vectors carrying a transgene encoding a polypeptide associated with a glycogen storage disease. By "associated with a glycogen storage disease", it is intended that the expressed polypeptide is one that is deficient or defective in a glycogen storage disease, or is otherwise a causative agent in a glycogen storage disease.

There are a multitude of glycogen storage diseases (GSD), as is recognized in the art. Exemplary glycogen storage diseases include, but are not limited to, Type Ia GSD (von Gierke disease), Type Ib GSD, Type Ic GSD, Type Id GSD, Type II GSD (including Pompe disease or infantile Type II GSD), Type IIIa GSD, Type IIIb GSD, Type IV GSD, Type V GSD (McArdle disease), Type VI GSD, Type VII GSD, glycogen synthase deficiency, hepatic glycogenosis with renal Fanconi syndrome, phosphoglucoisomerase deficiency, muscle phosphoglycerate kinase deficiency, phosphoglycerate mutase deficiency, and lactate dehydrogenase deficiency.

Polypeptides that are associated with glycogen storage diseases according to the present invention include, but are not limited to, glucose 6-phosphatase, lysosomal acid α glucosidase, glycogen debranching enzyme, branching enzyme, muscle phosphorylase, liver phosphorylase, phosphorylase kinase, muscle phosphofructokinase, glycogen synthase, phosphoglucoisomerase, muscle phosphoglycerate kinase, phosphoglycerate mutase, and lactate dehydrogenase.

In more preferred embodiments, a viral vector of the present invention carries a transgene encoding a lysosomal acid α-glucosidase (GAA), e.g., to treat Type II GSD including infantile (Pompe disease), juvenile and adult onset forms of the disease. More preferably, the lysosomal acid α-glucosidase is a human lysosomal acid α-glucosidase (hGAA). The transgene can encode either the mature GAA protein (e.g., the 76 kD form) or a GAA precursor (e.g., the 110 kD form). Preferably, the transgene encodes a GAA precursor. The term "GAA" as used herein encompasses mature and precursor GAA proteins as well as modified (e.g., mutated) GAA proteins that retain biological function (i.e., have at least one biological activity of the native GAA protein, e.g., can hydrolyze glycogen).

Lysosomal acid α-glucosidase (E.C. 3.2.1.20) (1,4-α-D-glucan glucohydrolase), is an exo-1,4-α-D-glucosidase that hydrolyses both α-1,4 and α-1,6 linkages of oligosaccharides liberating glucose. It catalyzes the complete degradation of glycogen with slowing at branching points. The 28 kb acid α-glucosidase gene on human chromosome 17 encodes a 3.6 kb mRNA which produces a 951 amino acid polypeptide (Hoefsloot et al., (1988) EMBO J. 7:1697; Martiniuk et al., (1990) DNA and Cell Biology 9:85). The nucleotide sequence of a cDNA coding for a GAA polypeptide, as well as the deduced amino acid sequence is provided in Hoefsloot et al., (Id.). The first 27 amino acids of the polypeptide are typical of a leader sequence of a signal peptide of lysosomal and secretory proteins. The enzyme receives co-translational N-linked glycosylation on the endoplasmic reticulum. It is synthesized as a 110-kDa precursor form, which matures by extensive modification of its glycosylation, by phosphorylation and by proteolytic processing through an approximately 90-kDa endosomal intermediate into the final lysosomal 76 and 67 kDa forms (Hoefsloot, (1988) EMBO J. 7:1697; Hoefsloot et al., (1990) Biochem. J. 272:485; Wisselaar et al., (1993) J. Biol. Chem. 268:2223; Hermans et al., (1993) Biochem. J. 289:681).

The human GM gene as described by Hoefsloot et al., (1988) EMBO J. 7:1697 and Van Hove et al., (1996) Proc. Natl. Acad. Sci. USA 93:65, includes 5' untranslated sequences. In particular preferred embodiments, the hGAA transgene includes the entire approximately 3.8 kb sequence described by Van Hove et al. Alternatively, a viral vector of the present invention can encode more or less of the 5' and 3' untranslated regions of the GAA gene.

Those skilled in the art will appreciate that the heterologous nucleotide sequence(s) are preferably operably associated with the appropriate expression control sequences. For example, the viral vectors of the invention preferably contain appropriate transcription/translation control signals and polyadenylation signals operably associated with the heterologous nucleic acid sequence(s) to be delivered to the target cell. Those skilled in the art will appreciate that a variety of promoter/enhancer elements can be used depending on the level and tissue-specific expression desired. The promoter can be constitutive or inducible (e.g., the metallothionine promoter or a hormone inducible promoter), depending on the pattern of expression desired. The promoter may be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest. Brain-specific, hepatic-specific, and muscle-specific (including skeletal, cardiac, smooth, and/or diaphragm-specific) promoters are more preferred. Also preferred are cancer cell specific promoters. Mammalian promoters are also preferred.

More preferably, the heterologous nucleotide sequence(s) are operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter. It has been speculated that driving heterologous nucleotide transcription with the CMV promoter results in down-regulation of expression in immunocompetent animals (see, e.g., Guo et al., (1996) Gene Therapy 3:802). Accordingly, it is also preferred to operably associate the heterologous nucleotide sequence(s) with a modified CMV promoter that does not result in this down-regulation of transgene expression.

In embodiments wherein there is more than one heterologous nucleotide sequence, those skilled in the art will appreciate that the heterologous nucleotide sequences may be operatively associated with a single upstream promoter and one or more downstream internal ribosome entry site (IRES) sequences (e.g., the picornavirus EMC IRES sequence).

In embodiments of the invention in which the heterologous nucleotide sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

IV.A. Gene Transfer Technology

The methods of the present invention provide an approach for delivering heterologous nucleotide sequences into a broad range of host cells, including both dividing and non-dividing cells in vitro or in vivo. The vectors, methods and pharmaceutical formulations of the present invention are additionally useful in a method of administering a therapeutic nucleic acid or therapeutic polypeptide to a subject in need thereof, as a method of treatment or otherwise. In this manner, the encoded nucleic acid or polypeptide is produced in vivo in the subject. For example, the subject might be in need of the polypeptide because the subject has a deficiency of the polypeptide, or because the production of the polypeptide in the subject imparts some therapeutic effect, as a method of treatment or otherwise, and as explained further below.

In general, the present invention can be employed to deliver any foreign nucleotide sequence to treat or ameliorate the symptoms associated with any disorder related to gene expression. Illustrative disease states include: lysosomal storage diseases, glycogen storage diseases, hemophilias (e.g., hemophilia A and hemophilia B) and other clotting disorders, Gaucher's Disease, diabetes mellitus, cystic fibrosis (and other diseases of the lung), muscular dystrophies (e.g., Duchenne, Becker), diseases of the nervous system (e.g., Alzheimer's Disease, Parkinson's Disease, amyotrophic lateral sclerosis, epilepsy), retinal degenerative diseases (and other diseases of the eye), diseases of solid organs (e.g., brain, liver, kidney, heart), and any other diseases having an infectious or genetic basis.

Alternatively, a viral vector may be administered that encodes any therapeutic polypeptide.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues to thereby replace lost function. Gene transfer can be used as well to create animal models for the disease using antisense mutations. Conversely, a therapeutic polypeptide comprising a dominant negative function can be used to treat disorders characterized by excessive gene function. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The instant invention can also be employed to provide an antisense nucleic acid to a cell in vitro or in vivo. Expression of the antisense nucleic acid in the target cell diminishes expression of a particular protein by the cell. Accordingly, antisense nucleic acids can be administered to decrease expression of a particular protein in a subject in need thereof. Antisense nucleic acids can also be administered to cells in vitro to regulate cell physiology, e.g., to optimize cell or tissue culture systems. The present invention is also useful to deliver other therapeutic nucleic acids, including but not limited to non-translated RNAs, e.g., ribozymes or "guide" RNAs (see, e.g., Gorman et al., (1998) *Proc. Nat. Acad. Sci. USA* 95:4929) to a target cell.

Finally, the instant invention finds further use in diagnostic and screening methods, whereby a gene of interest is transiently or stably expressed in a cell culture system.

The present invention is further useful for imaging methods. Viral vectors of the invention can further comprise a detectable label, preferably a label that is detectable in vivo. Thus, the methods of the present invention can further comprise detecting the detectable label, to thereby detect viral vectors following administration to a subject.

IV.B. Immunization Methods

As a further aspect, the present invention provides a method of producing an immune response in a subject, comprising administering a viral vector carrying a nucleotide sequence encoding an immunogen to a subject, and an active immune response is mounted by the subject against the immunogen. Immunogens are as described hereinabove. Preferably, a protective immune response is elicited.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

A viral vector expressing an immunogen may be administered directly to the subject, as described below.

Alternatively, a viral vector may be administered to a cell ex vivo and the altered cell is administered to the subject. The heterologous nucleotide sequence is permitted to be introduced into the cell, and the cell is administered to the subject, where the heterologous nucleotide sequence encoding the immunogen is preferably expressed and induces an immune response in the subject against the immunogen. Preferably, the cell is an antigen presenting cell (e.g., a dendritic cell) or a cancer.

According to the foregoing methods of inducing an immune response in a subject, it is preferred that a viral vector carrying the heterologous nucleotide sequence is administered in an immunogenically effective amount, as described below.

As described in more detail below, the present invention also encompasses methods of treating cancer using immunotherapy by administration of Ad vectors expressing cancer cell antigens or any other immunogen that produces an immune response against a cancer cell. In one particular embodiment, an immune response may be produced against a cancer cell antigen in a subject by administering a viral vector comprising a heterologous nucleotide sequence encoding the cancer cell antigen, for example to treat a patient with cancer. The viral vector may be administered to a subject in vivo or by using ex vivo methods, as described herein.

IV.C. Methods of Treating Cancer

As used herein, the term "cancer" encompasses tumor-forming cancers. Likewise, the term "cancerous tissue" encompasses tumors. A "cancer cell antigen" encompasses tumor antigens.

In particular embodiments, the inventive viral vectors are administered as part of a method of treating cancer by administering anti-cancer agents (e.g., cytokines) or a cancer cell antigen or other immunogen that produces an immune response against a cancer cell. A viral vector may be administered to a cell in vitro or to a subject in vivo or by using ex vivo methods, as described herein and known in the art.

The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. Preferred are methods of treating and preventing tumor-forming cancers.

The term "tumor" is also understood in the art, for example, as an abnormal mass of undifferentiated cells within a multicellular organism. Tumors can be malignant or benign. Preferably, the inventive methods disclosed herein are used to prevent and treat malignant tumors.

Cancer cell antigens according to the present invention have been described hereinabove. By the terms "treating cancer" or "treatment of cancer", it is intended that the severity of the cancer is reduced or the cancer is at least partially eliminated. Preferably, these terms indicate that metastasis of the cancer is reduced or at least partially eliminated. It is further preferred that these terms indicate that growth of metastatic nodules (e.g., after surgical removal of a primary tumor) is reduced or at least partially eliminated. By the terms "prevention of cancer" or "preventing cancer" it is intended that the inventive methods at least partially eliminate or reduce the incidence or onset of cancer. Alternatively stated, the present methods slow, control, decrease the likelihood or probability, or delay the onset of cancer in the subject.

In particular embodiments, cells may be removed from a subject with cancer and contacted with the viral vectors of the invention. The modified cell is then administered to the subject, whereby an immune response against the cancer cell antigen is elicited. This method is particularly advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, in particular embodiments of the invention, immunomodulatory cytokines (preferably, CTL inductive cytokines) are administered to a subject in conjunction with the methods described herein for producing an immune response or providing immunotherapy.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

IV.D. Subjects, Pharmaceutical Formulations, Vaccine and Modes of Administration The present invention finds use in veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include neonates, infants, juveniles, and adults.

In particular embodiments, the present invention provides a pharmaceutical composition comprising a virus particle of the invention in a pharmaceutically-acceptable carrier and, optionally, other medicinal agents, pharmaceutical agents, carriers, adjuvants, diluents, and the like. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In general, a "physiologically acceptable carrier" is one that is not toxic or unduly detrimental to cells. Exemplary physiologically acceptable carriers include sterile, pyrogen-free water and sterile, pyrogen-free, phosphate buffered saline. Physiologically-acceptable carriers include pharmaceutically-acceptable carriers.

By "pharmaceutically acceptable" it is meant a material that is not biologically or otherwise undesirable, i.e., the material may be administered to a subject along with the viral vector without causing any undesirable biological effects. Thus, such a pharmaceutical composition can be used, for example, in transfection of a cell ex vivo or in administering a viral particle directly to a subject.

One aspect of the present invention is a method of transferring a nucleotide sequence to a cell. The virus particles may be added to the cells at the appropriate multiplicity of infection according to standard transduction methods appropriate for the particular target cells. Titers of virus to administer can vary, depending upon the target cell type and the particular virus vector, and can be determined by those of skill in the art without undue experimentation. Preferably, at least about $10^3$ infectious units, more preferably $10^4$ infectious units, even more preferably at least about $10^5$ infectious units, are administered to the cell. In another embodiment quantities for the number of AAV vector particles (e.g. AAV6 particles) administered per cell can range from about 100 to about 10,000 particles per cell, including about 250, about 500, about 1,000, and about 5,000.

Alternatively, administration of a viral vector of the present invention can be accomplished by any other means known in the art. For example, viral vectors can be targeted to cells, including cells that are not normally competent for transduction by adenoviruses using antibodies, e.g., as described in U.S. Pat. No. 5,861,156 to George et al.; U.S. Pat. No. 5,521, 291 to Curiel et al., the disclosures of which are incorporated herein in their entirety by reference. Alternatively, adenoviruses can be targeted to cell-surface proteins (e.g., receptors) by expressing a binding protein or ligand on the surface of the adenovirus, e.g., as described by Douglas et al., (1996) Nature Biotechnology 14:1574; U.S. Pat. No. 5,770,442 to Wickham et al.; and U.S. Pat. No. 5,712,136 to Wickham et al. (the disclosures of which are all incorporated herein in their entirety).

The cell to be administered the inventive virus vectors can be of any type, including but not limited to neuronal cells (including cells of the peripheral and central nervous systems), retinal cells, epithelial cells (including dermal, gut, respiratory, bladder and breast tissue epithelium), muscle cells (including cardiac, smooth muscle, skeletal muscle, and diaphragm muscle), pancreatic cells (including islet cells), hepatic cells (e.g., parenchyma), fibroblasts, endothelial cells, germ cells, lung cells (including bronchial cells and alveolar cells), prostate cells, stem cells, progenitor cells, dendritic cells, and the like. Alternatively, the cell is a cancer cell (including tumor cells). Moreover, the cells can be from any species of origin, as indicated above. Preferred are cells that are naturally transduced by adenoviruses.

The viral vectors of the invention may be employed to produce polypeptides of interest by cells in vitro. The adenovirus comprises a heterologous nucleotide sequence(s) that may encode any polypeptide of interest, as described hereinabove. The nucleotide sequence preferably encodes a therapeutic polypeptide or an industrial protein (i.e., for use in an industrial process). In more preferred embodiments, the heterologous nucleotide sequence encodes a GAA, more preferably human GAA, which may be isolated from the cells using standard techniques and administered to subjects with GAA deficiency using enzyme replacement protocols (see, e.g., Van der Ploeg et al., (1991) J. Clin. Invest. 87:513).

In particular embodiments of the invention, the cell has been removed from a subject, the viral vector is introduced therein, and the cells are then replaced back into the subject. Methods of removing cells from subjects for treatment ex vivo, followed by introduction back into the subject are known in the art (see, e.g., U.S. Pat. No. 5,399,346; the disclosure of which is incorporated herein in its entirety). As a further alternative, the cells that are manipulated and then introduced into the subject are provided from another subject or cell line.

A further aspect of the invention is a method of treating subjects in vivo with the inventive virus particles. Administration of the viral particles of the present invention to a human subject or an animal in need thereof can be by any apprpoach known in the art for administering virus vectors. Preferably, at least about 1000, more preferably, at least about 10,000 infectious units are administered to the subject per treatment. Preferably, the subject is a mammalian subject, more preferably a human subject. Also preferred are subjects that have been diagnosed with a lysosomal storage disease or a glycogen storage disease. More preferred are subjects who have been diagnosed with GAA deficiency. Also preferred are subjects with cancer.

In one embodiment, a method of introducing a nucleic acid in accordance with the present invention comprises contacting a cell with a recombinant hybrid virus of the present invention under conditions sufficient for entry of the recombinant virus particle into the cell, and further comprises introducing an AAV Rep 68/78 protein or sequences encoding an AAV Rep 68/78 protein into the cell. Preferably, the cell comprises a human cell present in vitro, ex vivo, or in vivo. Thus, in this embodiment, site-specific integration into human chromosome 19 in cells or in vivo can be accomplished by providing AAV Rep 68/78 protein (or sequences encoding the same) as part of or along with a hybrid vector of the present invention. General guidance as to the practice of this embodiment can be found in Recchia, A., et al., Proc Nat Acad Sci USA 96:2615-2620.

Continuing with this embodiment, a hybrid vector is optionally c-administered with a vector comprising inducible AAV rep68/78 sequences. Preferably, the second vector does not include AAV rep48/52 sequences. Thus, the sequences encoding the AAV Rep 68/78 protein are operably associated with an inducible promoter. The inducible promoter can comprise any of the inducible promoters disclosed herein, but preferably comprises a tetracycline response element. A vector encoding an inducible AAV Rep 68/78 can comprise any of the vectors disclosed herein, but is preferably one of a plasmid vector and an adenovirus vector. In the case of the use of an adenovirus vector, it is preferred that the hybrid vector and the vector encoding Rep 68/78 be delivered to a liver cell in accordance with techniques disclosed herein. Indeed, through the use of an adenovirus vector as the second vector, long-term delivery of a gene to about 100% of cells in the liver is provided.

Dosages will depend upon the mode of administration, the disease or condition to be treated, the individual subject's condition, the particular virus vector, and the gene to be delivered, and can be determined in a routine manner. Preferably, at least about $10^5$ infectious units of the inventive viral vectors are administered to the subject. Exemplary doses for achieving therapeutic effects are virus titers of $10^8$-$10^{14}$ particles, preferably $10^{10}$-$10^{13}$ particles, yet more preferably about $10^{12}$ particles.

In another embodiment quantities for the number of AAV vector particles (e.g. AAV6 particles) administered per cell can range from about 100 to about 10,000 particles per cell, including about 250, about 500, about 1,000, and about 5,000.

A "therapeutically-effective" amount as used herein is an amount that provides sufficient expression of the heterologous nucleotide sequence delivered by the vector to provide some improvement or benefit to the subject. Alternatively stated, a "therapeutically-effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

In particular embodiments of the invention, more than one administration (e.g., two, three, four, or more administrations) may be employed to achieve therapeutic levels of gene expression.

Vaccines of the present invention comprise an immunogenic amount of infectious virus particles as disclosed herein in combination with a pharmaceutically-acceptable carrier. An "immunogenic amount" is an amount of the infectious virus particles that is sufficient to evoke an immune response in the subject to which the pharmaceutical formulation is administered. An amount of from about $10^2$ to about $10^9$ virus particles, preferably from about $10^3$ to about $10^7$ virus particles, and more preferably about $10^4$ to $10^6$ virus particles per dose may be suitable, depending upon the age and species of the subject being treated, and the immunogen against which the immune response is desired. Other appropriate doses of the inventive virus particles for producing a desired immune response may be routinely determined by those skilled in the art.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue (e.g., muscle) or organ injection (e.g., into the liver, into the brain for delivery to the central nervous system), alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

In particularly preferred embodiments of the invention, the viral vector comprising a heterologous nucleic acid sequence of interest is delivered to the liver of the subject. Administration to the liver can be achieved by any method known in the art, including, but not limited to intravenous administration, intraportal administration, intrabiliary administration, intraarterial administration, and direct injection into the liver parenchyma. Intramuscular delivery to skeletal muscle is also preferred.

The viral vectors disclosed herein may alternatively be administered to the lungs of a subject by any suitable means, but are preferably administered by administering an aerosol suspension of respirable particles comprised of the inventive viral vectors, which the subject inhales. The respirable particles may be liquid or solid. Aerosols of liquid particles comprising the inventive viral vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the inventive virus vectors may likewise be produced with any solid particulate medicament aerosol generator, by techniques known in the pharmaceutical art.

In particular embodiments, a viral vector encoding a polypeptide is introduced into target cells (e.g., liver cells or skeletal muscle cells) and the polypeptide is expressed therein, and optionally secreted into the circulatory system, where it is delivered to target tissues, preferably, in a therapeutic amount. Intramuscular delivery to skeletal muscle or delivery to the liver are preferred in the practice of this embodiment of the invention.

EXAMPLES

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the invention.

Example 1

Cell Culture 293 cells, C-7 cells (Amalfitano et al. (1999) *Proc. Natl. Acad. Sci. U.S.A.* 96:8861-8866), and GSD II patient fibroblasts were maintained in Dulbecco's modified Eagle medium supplemented with 10% fetal bovine serum, 100 U penicillin per milliliter, and 100 µg streptomycin per milliliter at 37° C. in a 5% $CO_2$-air atmosphere. C-7 cells were grown in the presence of hygromycin, 50 µg/ml. HeLa cells were maintained in minimum essential medium Eagle supplemented with 10% fetal bovine serum, 1 mm minimum essential medium sodium pyruvate, 0.1 mm minimum essential medium non-essential amino acids, 100 U penicillin per milliliter, and 100 µg streptomycin per milliliter at 37° C. in a 5% $CO_2$-air atmosphere.

Example 2

Transduction of Cultured Cells

HeLa cells and GSD II fibroblasts were plated at $1 \times 10^6$ cells per 150 mm tissue culture dish. Cells were transduced the next day by adding a volume of the respective vector stock containing 1,000, 10,000, or 50,000 DNase I-resistant vector particles (as defined by Southern blot analysis) per cell. Cells were harvested five days later for hGAA measurement and Western blotting analysis.

Example 3

Construction of an AAV Vector Plasmid Encoding hGAA

The hGAA cDNA was subcloned with the CMV promoter from pcDNA3-hGAA (Van Hove et al. (1996) *Proc. Natl. Acad. Sci. U.S.A.* 93:65-70) into an AAV vector plasmid to generate pAAV-CBGAApA. The vector sequences from pAAV-CBGAApA were isolated as a 4.4 kbp fragment from a partial BglII digest, and ligated with the calf intestinal alkaline phosphatase-dephosphorylated BglII site of pShuttle (He et al. (1998) *Proc. Nat. Acad. Sci. U.S.A.* 95:2509-2514).

Example 4

Construction of a Hybrid [E1-,polymerase-, preterminal protein-1-]Ad-AAV Vector Encoding hGAA Kanamycin-resistant shuttle plasmids were constructed to contain within the Ad E1 region the CB promoter+hGAA cDNA+polyA transgene cassette flanked by the AAV2 TR sequences. The shuttle plasmid was digested with PmeI, and electroporated into the BJ5183 recombinogenic strain of *E. coli* with the pAd[E1-,polymerase-, preterminal protein-] plasmid (Amalfitano et al. (1998) *J. Virol.* 72:926-933). Recombinant kanamycin-resistant clones were screened by restriction enzyme digestion (BstXI) to confirm successful generation of the full length recombinant Ad vector genomes. These clones were digested with PacI and transfected as previously described into the E1, and E2b expressing cell line, C-7 (Amalfitano et al. (1998) *J. Virol.* 72:926-933). The vectors was amplified and confirmed to have the correct construction by restriction enzyme mapping of vector genomes, and subsequent functional assays in vitro and in vivo.

Once isolated, the respective Ad vectors are serially propagated in increasing numbers of C-7 cells (Hodges et al. (2000) *J. Gene Med.* 2:250-259). Forty-eight hours after infection, infected cell pellets were harvested by low speed centrifugation, resuspended in 10 mM Tris-HCl pH=8.0, vector released from the cells by repeated freeze-thawing (3 times) of the lysate and by ultrasonification, and the vector containing supernatant subjected to two rounds of equilibrium density CsCl centrifugation (Amalfitano et al. (1998) *J. Virol.* 72:926-933). Two virus bands were visible. The virus bands were then removed, dialyzed extensively against 10 mm Tris-HCl pH=8.0 (or PBS), sucrose added to 1%, and aliquots stored at −80° C. The number of vector particles was quantified based on the $OD_{260}$ of vector contained in dialysis buffer with sodium dodecyl sulfate [SDS] disruption (Ding et al. (2001) Hum. Gene Ther. 12:955-965), and by DNase I digestion, DNA extraction, and Southern blot analysis.

Hybrid AD-AAV vector DNA analysis included vector DNA isolation and restriction enzyme digestion followed by Southern blotting to verify the presence of intact AAV vector sequences, including restriction enzymes that demonstrate the presence of AAV terminal repeat sequences flanking the transgene (AhdI and BssHII).

Example 5

Preparation of AAV Vectors

AAV vector stocks were prepared as described with modifications (Allen et al. (2000) Mol. Ther. 1:88-95, Conway et al. (1999) Gene Ther. 6:986-993). 293 cells were transduced with the hybrid Ad-AAV vector (2000 DNase I-resistant vector particles/cell as quantitated by Southern blot analysis) containing the AAV vector sequences 15-30 minutes before transfection with a AAV packaging plasmids containing the AAV2 Rep and Cap genes driven by heterologous promoters, which typically generate no detectable replication-competent AAV (rcAAV) (Allen et al. (2000) Mol. Ther. 1:88-95). For the transfection-only method (modified from Allen et al. (2000) Mol. Ther. 1:88-95), pLNCorf6 (Hadjigeorgiou et al. (1999) J. Inherit. Metab. Dis. 22:762-763) provided E4orf6 gene which is an essential Ad helper function for AAV packaging, and no Ad or Ad-AAV vector was required. Cell lysate was harvested 48 hours following infection and freeze-thawed 3 times, isolated by iodoxinal step gradient centrifugation before heparin affinity column purification (Zolotukhin et al. (1999) Gene Ther. 6:973-985), and aliquots stored were at −80° C.

The number of vector DNA containing-particles was determined by DNase I digestion, DNA extraction, and Southern blot analysis. Contaminating wt AAV particles were detected in recombinant AAV vector preparations by Southern blot analysis of extracted vector DNA, and by a sensitive PCR assay utilizing primers spanning the junction between the rep and cap genes. The level of rcAAV was less than 1 particle in $10^5$ AAV vector particles. All viral vector stocks were handled according to Biohazard Safety Level 2 guidelines published by the NIH.

Example 6

In Vivo Administration of Hybrid Ad-AAV and AAV Vector Stocks

The vector was administered intravenously (via the retro-orbital sinus) into 6-week-old GAA-KO mice (Raben et al. (1998) J. Biol. Chem. 273:19086-19092). Either $2\times10^{10}$ DNase I-resistant Ad-AAV, $4\times10^{10}$ AAV, or $1\times10^{12}$ AAV vector particles were injected per animal. At the respective time points post-injection, plasma or tissue samples were obtained and processed as described below. All animal procedures were done in accordance with Duke University Institutional Animal Care and Use Committee-approved guidelines (Duke University, Durham, N.C., United States of America).

Example 7

Determination of hGAA Activity

Liver hGAA activity was measured following removal of the liver from control or treated mice, flash-freezing on dry ice, homogenization and sonication in distilled water, and pelleting of insoluble membranes/proteins by centrifugation. The protein concentrations of the clarified suspensions were quantified via the Bradford assay. hGAA activity in the liver was determined as described (Amalfitano et al. (1999) Proc. Natl. Acad. Sci. U.S.A. 96:8861-8866). Cellular hGAA was measured in transduced and control HeLa cells following scraping, washing with PBS, suspension in and sonic disruption in distilled water, and pelleting of insoluble membranes/proteins by centrifugation. The protein concentrations of the clarified suspensions were quantified via the Bradford assay, and hGAA activity was determined as described (Amalfitano et al. (1999) Proc. Natl. Acad. Sci. U.S.A. 96:8861-8866).

Example 8

Western Blotting Analysis of hGAA

For direct detection of hGAA in liver, the liver was flash-frozen on dry ice, homogenized and sonically disrupted in distilled water, and insoluble membranes/proteins were pelleted by centrifugation. The protein content of the supernatants were measured by the Bradford assay. Samples (100 μg of protein) were electrophoresed overnight in a 6% polyacrylamide gel to separate proteins, and transferred to a nylon membrane. The blots were blocked with 5% nonfat milk solution, incubated with primary and secondary antibodies and visualized via the enhanced chemiluminescence (ECL) detection system (Amersham Pharmacia, Piscataway, N.J., United States of America) (Ding et al. (2001) Hum. Gene Ther. 12:955-965).

Example 9

Markedly Enhanced AAV Vector Packaging with a Hybrid Ad-AAV Vector

Figure 1B:
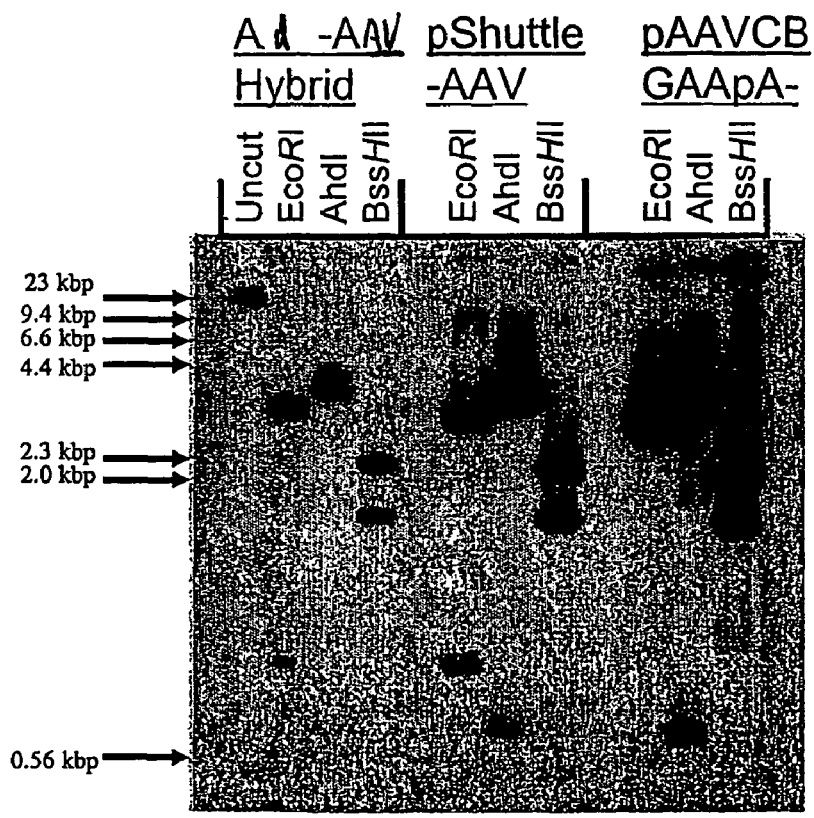
FIG. 1B is an autoradiograph depicting Southern blot analysis of DNase I-resistant hybrid Ad-AAV vector particles (Ad-AAV hybrid), the plasmid containing the AAV vector sequences prior to bacterial recombination to produce Ad particles (pShuttle-AAV), and the AAV vector plasmid (pAAVCBGAApA). DNA was analyzed with AhdI and BssHII to determine that the AAV TR sequences were present (not deleted during recombination). AhdI cuts once in each terminal repeat and BssHII cuts twice in each terminal repeat, and each restriction digest gives unique fragments that were present in the recombinant Ad-AAV DNA.
Figure 1C:
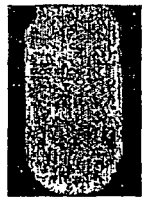
FIG. 1C is a photograph of a cesium chloride gradient of hybrid Ad-AAV vector particles. Two viral bands were present, which eqilibrated at positions below a layer of protein at the top of the gradient.
Figure 1D:
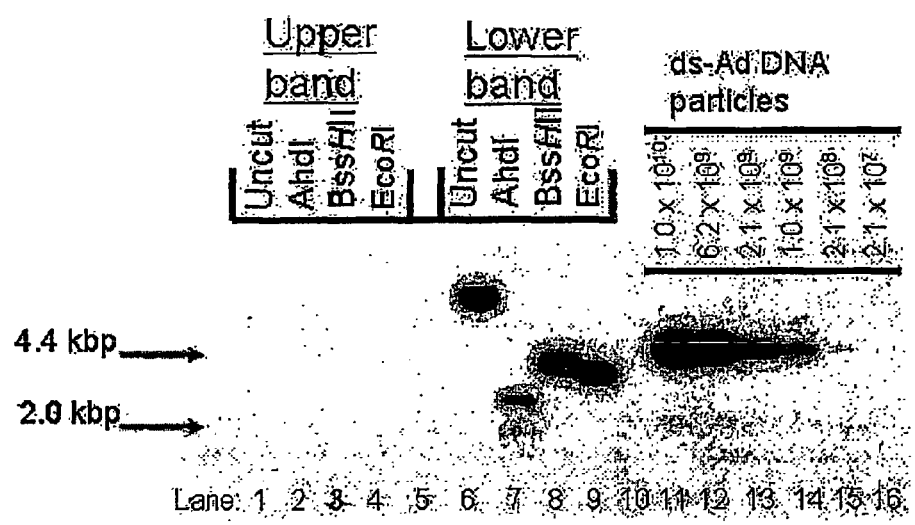
FIG. 1D is an autoradiograph depicting Southern blot analysis of the two viral bands in FIG. 1C. Vector DNA was treated with DNase I and extracted prior to restriction enzyme analyis and Southern blotting. Each sample was 10 μl. Lanes (11)-(16) contain linearized Ad5-containing plasmid representing the indicated number of double-stranded (ds) Ad particles. Therefore, the vector stock purified from the lower band contained $3.1 \times 10^{11}$ DNase I-resistant Ad-AAV vector particles per ml (lanes 6-9).
Figure 1E:
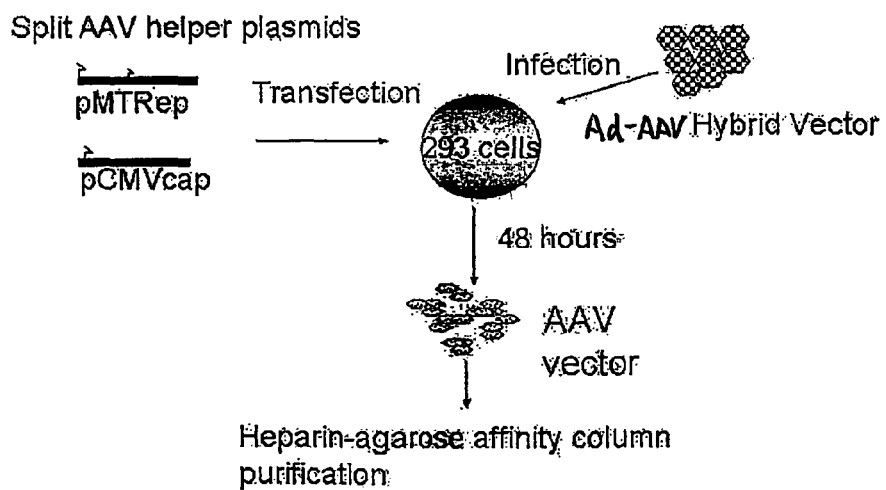
FIG. 1E is a schematic of a hybrid Ad-AAV vector packaging method for AAV vector purification. 293 cells were transfected with split AAV helper plasmids and transduced with a hybrid Ad-AAV vector containing the AAV vector sequences. No contaminating modified Ad vector is replicated by 293 cells (Amalfitano et al. (1998) *J. Virol.* 72:926-933). The AAV vector was purified by heparin-agarose column method (Zolotukhin et al. (1999) *Gene Ther.* 6:973-985).

An AAV vector sequence was cloned into a multiply-deleted, replication-deficient adenovirus, such that it is packaged as an adenovirus vector (FIG. 1A). The hybrid vector, Ad-AAV-CBGAApA, was constructed with the bacterial recombination system (He et al. (1998) Proc. Nat. Acad. Sci. U.S.A. 95:2509-2514). The plasmid containing the long arm of adenovirus was modified by deletion of the E1, polymerase (pol), and preterminal protein (pTP) genes, such that the Ad-AAV vector carried the deletion and was replication-deficient in 293 cells (Amalfitano et al. (1998) J. Virol. 72:926-933). Following two rounds of equilibrium density cesium chloride centrifugation, 2 Ad-AAV bands were visible; however, no vector DNA could be isolated from the upper, lower-density Ad-AAV band in the cesium gradient (FIG. 1C), as detected by Southern blot analysis with either Ad5 or hGAA probes (FIG. 1D). The restriction sites within the TR sequences were intact as determined by restriction enzyme digestion with AhdI and BssHII (FIG. 1B and FIG. 1D), and DNase-I resistant hybrid Ad-AAV vector particles were quantitated versus a standard curve of plasmid DNA (FIG. 1D). The Ad-AAV vector generated high levels of hGAA in transduced HeLa cells (Table 1). Thus, it was confirmed that the hybrid Ad-AAV vector contained both the AAV vector sequences and the adenovirus helper functions required to package an AAV vector (FIG. 1E).

Example 10

Analysis of Different Packaging Conditions

TABLE 1

Enzyme analysis of transduced HeLa cells.

| Vector | No vector | $10^2$ vector particles/ cell | $10^3$ vector particles/ cell | $10^4$ vector particles/ cell | $5 \times 10^4$ vector particles/ cell |
|---|---|---|---|---|---|
| No vector | 34.5 +/− 17.7 | N.A.[1] | N.A. | N.A. | N.A. |
| Ad-AAV-CBGAApA | NA | 43.4 +/− 2.5 | 189.3 +/− 27.1 | N.D. | N.D. |
| AAV-CBGAApA | N.A. | N.D. | 74.4 +/− 10.2 | 106.3 +/− 25.5 | 394.2 +/− 79.4 |

[1]Not applicable.
[2]Not done.

For an AAV Vector in 293 Cells

Figure 2A:
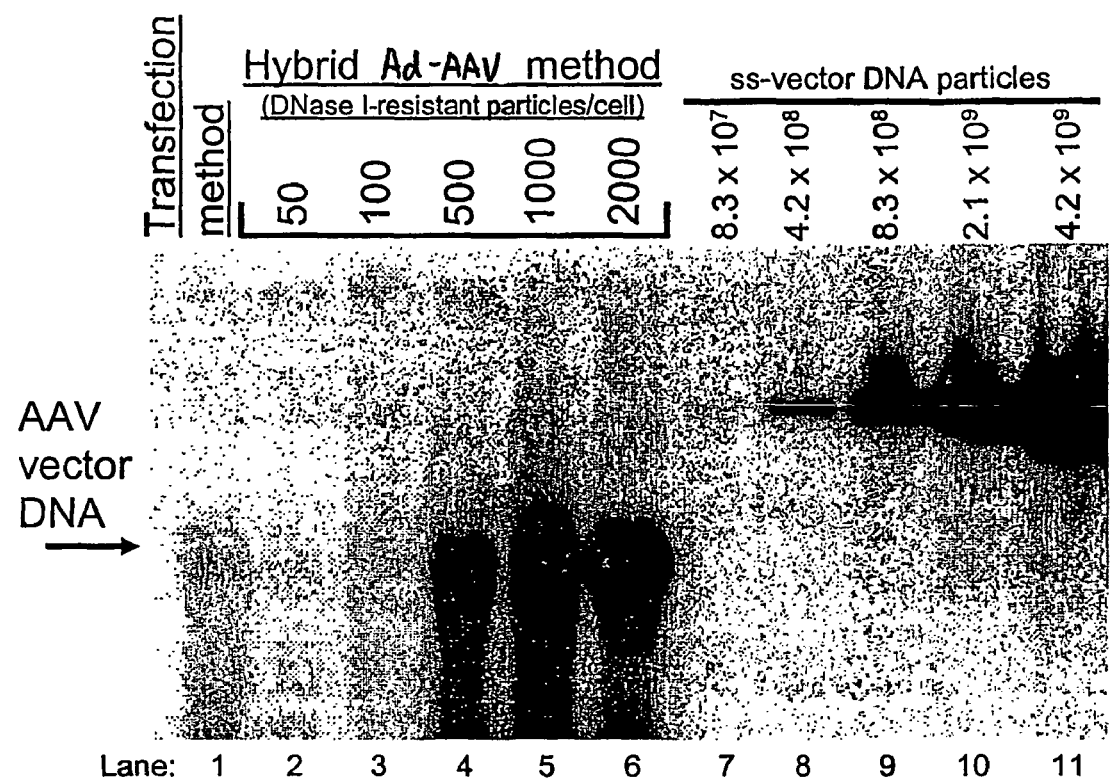
FIG. 2A is an autoradiograph of a Southern blot depicting AAV vector packaging with an Ad-AAV hybrid vector. For the transfection-only method, 293 cells were transfected with plasmids containing the AAV rep and cap genes driven by heterologous promoters (Allen et al. (2000) *Mol. Ther.* 1:88-95) and with the AAV vector plasmid and pLNCorf6 (Scaria et al. (1995) *Gene Ther.* 2:295-298) (lane 1 only). For the hybrid Ad-AAV method of AAV vector packaging, the cells were transduced with the indicated number of hybrid Ad-AAV vector DNase-I resistant particles, and transfected with plasmids containing the AAV rep and cap genes (as shown in FIG. 1D). The Southern blot shows the yield of DNase I-resistant single-stranded AAV vector genomes per cell for each condition. Each sample represented $6 \times 10^5$ 293 cells. Lanes (7) to (11) contained vector plasmid, digested with BgIII to release the double-stranded AAV vector sequences, representing the indicated number of single-stranded (ss) AAV vector particles.

The AAV vector packaging efficiency increased approximately 30-fold for the hybrid Ad-AAV method (as shown in FIG. 1D), because the yield for this particular vector increased from 1,300 particles per cell with a transfection-only method (modified from Allen et al. (1997) *J. Virol.* 71:6816-6822) to 38,000 DNase I-resistant particles per cell (FIG. 2A). Southern blot analysis of AAV vector DNA demonstrated an identical signal for the vector DNA fragment packaged with either the hybrid Ad-AAV or transfection-only method (FIG. 2A).

Figure 2B:
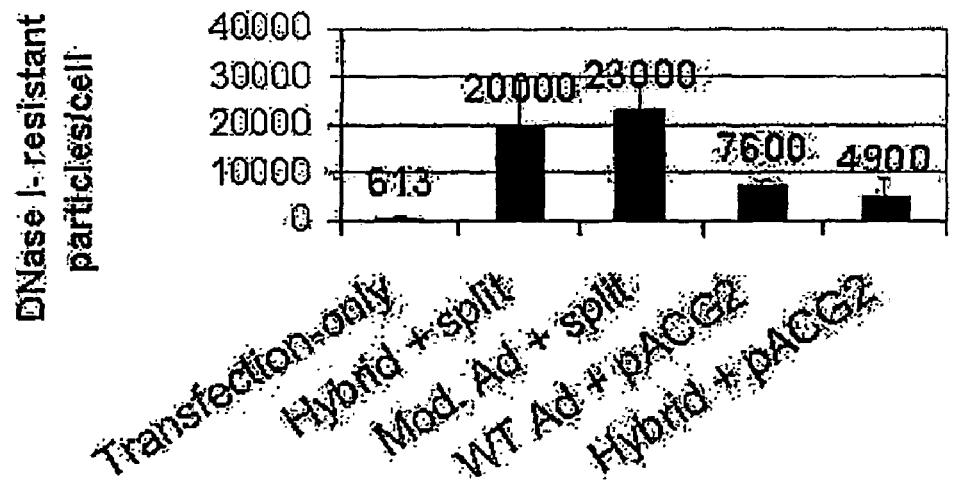
FIG. 2B is a bar graph showing that AAV-CBGAApA was packaged with different Ad and AAV helpers. Five conditions for packaging of AAV-CBGAApA were evaluated, including transfection of pAAV-CBGAApA plus split AAV helper plasmids and pLNCorf6 (adapted from Allen et al., 2000), hybrid Ad-AAV transduction plus transfection of split AAV helper plasmids, modified Ad ([E1-,polymerase-]AdCMVLacZ) transduction plus split transfection of split AAV helper plasmids, wild-type Ad5 infection plus tranfection of pACG2 (Xiao et al. (1998) *J. Virol.* 72:10222-10226) and pAAV-CBGAApA, and hybrid Ad-AAV transduction plus transfection of pACG2.

The relative efficiency of AAV vector packaging with 5 different helper-gene combinations in 293 cells was evaluated in order to elucidate factors underlying the hybrid Ad-AAV vector method (FIG. 2B). High levels of AAV vector packaging was observed for transduction with the hybrid Ad-AAV vector combined with transfection of split AAV helper plasmids (Allen et al. (1997) *J. Virol.* 71:6816-6822), which again showed a 33-fold increase in vector particles/cell compared to the transfection-only method. Transduction with an [E1-, polymerase-]Ad vector encoding β-galactosidase (Amalfitano, A., et al. (1998) *J. Virol.* 72: 926-933) also generated high numbers of AAV vector particles, when combined with transfection with split AAV helper plasmids encoding Rep and Cap (Allen et al. (2000) *Mol. Ther.* 1:88-95) and the AAV vector plasmid (pAAV-CBGAApA). Either infection with a wild-type Ad5 or transduction with the hybrid Ad-AAV vector, combined with transfection with pACG2 (Xiao et al. (1998) *J. Virol.* 72:10222-10226) (an AAV packaging plasmid) and the AAV vector plasmid (with wild-type Ad 5 only), demonstrated an intermediate efficiency of AAV vector packaging (FIG. 2B). Northern blot analysis of E4orf6 and E1A transcripts showed equivalent levels of E1a and E4orf6RNAs under the 5 conditions analyzed, suggesting a critical role for at least one additional Ad gene in the packaging of AAV-CBGAApA. The Ad gene(s) in question were provided by the second-generation Ad-AAV, [E1a-, polymerase-] Ad vector or wild-type Ad5, but not by pLNCorf6 alone (Scaria et al. (1995) *Gene Ther.* 2:295-298) during the transfection-only method.

Figure 2C:
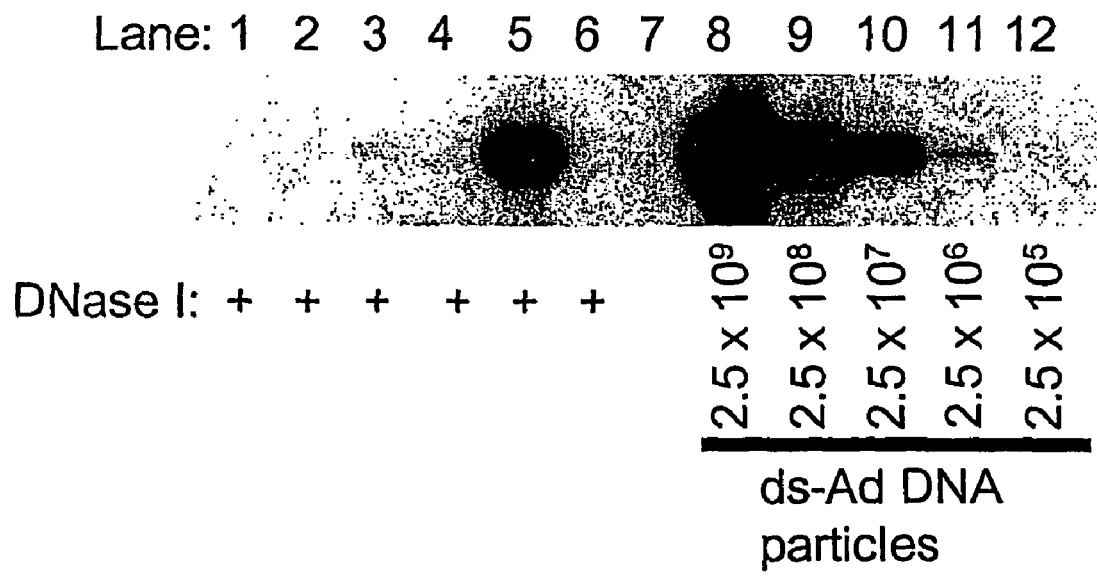
FIG. 2C is an autoradiograph of a Southern blot that was performed to quantify the contaminating Ad-AAV genomes. Lanes as follows: (1) untreated 293 cells, (2) transfection of pMV-CBGAApA plus split AAV helper plasmids and pLNCorf6 (adapted from Allen et al. 2000), (3) hybrid Ad-AAV transduction plus transfection of split AAV helper plasmids, (4) modified Ad ([E1-,polymerase-]AdCMVLacZ) transduction plus split transfection of split AAV helper plasmids, (5) wild-type Ad5 infection plus tranfection of pACG2 (Xiao et al. (1998) *J. Virol.* 72:10222-10226) and pAAV-CBGAApA, and (6) hybrid Ad-AAV transduction plus transfection of pACG2, (7) no sample, and (8)-(12) linearized Ad5-containing plasmid representing the indicated number of double-stranded (ds) Ad particles. Each sample represented 6×10⁵ 293 cells.

High molecular weight Ad-AAV DNA was present at low levels in the AAV vector stock at less than 1 Ad-AAV particle in 9,800 DNase I-resistant AAV particles, which hybridized with a probe containing sequence from the right arm of Ad5 (FIG. 2C, lanes 3, 4 and 6). By contrast, Ad5 produced >8,000 contaminating Ad DNase-resistant particles/cell during AAV vector packaging (FIG. 2C, lane 5). Thus, the level of contaminating Ad was reduced markedly by the use of a second-generation hybrid Ad-AAV (or Ad) vector that did not replicate in 293 cells to provide Ad helper functions.

Figure 3A:
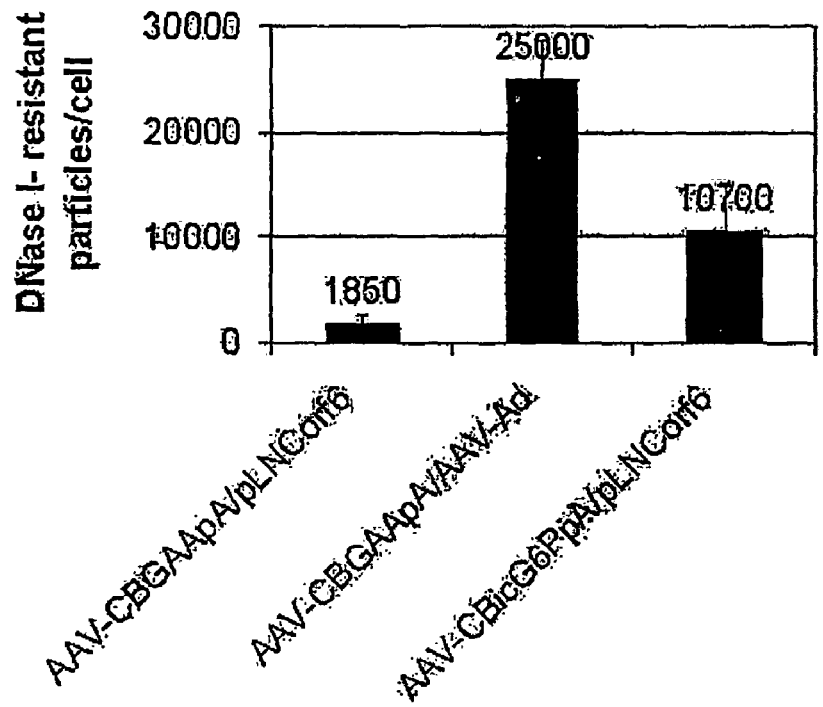
FIG. 3A is a bar graph depicting analysis of large-scale AAV vector packaging with an Ad-AAV hybrid vector. The yield of DNase I-resistant AAV vector particles for AAV-CBGAApA packaged by transfection of pLNCorf6, or transduction with the Ad-AAV hybrid to provide Ad helper functions, compared to a vector encoding glucose-6-phosphatase, AAV-CBcG6PpA, packaged with pLNCorf6. Twenty to 40 plate vector preparations were purified (3 vector preparations per condition), and the yield was calculated per cell plated. The mean number of AAV vector particles per cell is shown with the standard deviation indicated.

The yields for large-scale preparations of AAV-CBGAApA with the hybrid Ad-AAV packaging method were compared to previous results for the transfection-only method (FIG. 3A). The number of particles/cell for AAV-CBGAApA was elevated approximately 14-fold for the hybrid Ad-AAV packaging method (AAV-CBGAApA/Ad-AAV) compared to the transfection-only method (AAV-CBGAApA/pLNCorf6). The yield of AAV-CBcG6PpA for the transfection-only method was higher than expected based on the small-scale vector preparations described above. These variations could reflect higher-efficiency transfections with the transfection-only method during large-scale vector preparations. The packaging of another vector encoding canine G6 Pase, AAV-CBcG6PpA, was increased 5.8-fold compared to packaging AAV-CBGAApA with the transfection-only method. The relatively low yield of AAV-CBGAApA with the transfection-only method compared to AAV-CBcG6PpA suggested an effect related to packaging size constraints, since the packaging size for AAV-CBGAApA is approximately 1 kbp larger than for AAV-CBcG6PpA. However, the packaging size for AAV-CBGAApA was 4.4 kbp, within the optimal size for packaging in an AAV vector (Dong et al. (1996) *Gene Ther.* 7:2101-2112).

Figure 3B:
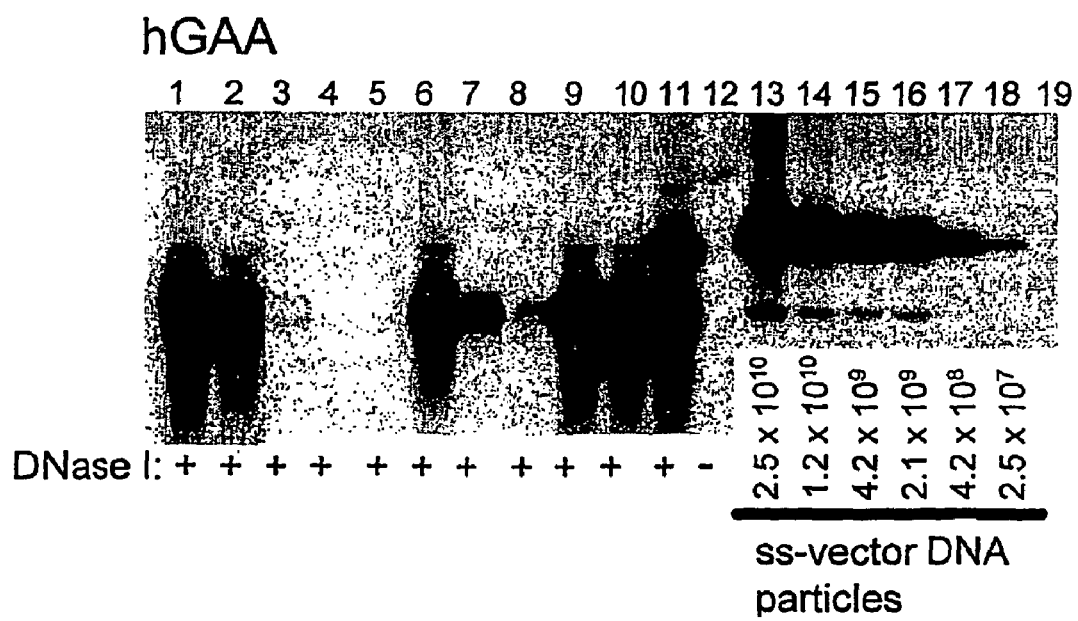
FIG. 3B is an autoradiograph of a Southern blot analysis of AAV-CBGAApA purification, quantified versus titrated vector plasmid DNA. The samples represent vector DNA extracted from 25 microliters of sample. Standard amounts of vector plasmids were loaded for quantitation of vector particles. Lanes represent the following samples: (1) Crude cell lysate, (2) 40% iodoxinal fraction (3) Heparin-agarose (HA) column flow-through, (4) HA column wash, (5) HA column eluate fraction (ef) 1, (6) HA column ef 2, (7) HA column ef 3, (8) HA column ef 4, (9) HA column ef 2 after dialysis (10) HA column ef 2 plus 2.5×10¹⁰ particles AAV vector plasmid, (11) HA column ef 2 plus 2.5×10¹⁰ particles AAV vector plasmid, no DNase I added, (12)-(18) vector plasmid representing the indicated number of single-stranded (ss) AAV vector particles. Therefore, the purified AAV vector stock contained 4.8×10¹¹ DNase I-resistant vector particles per ml.
Figure 3C:
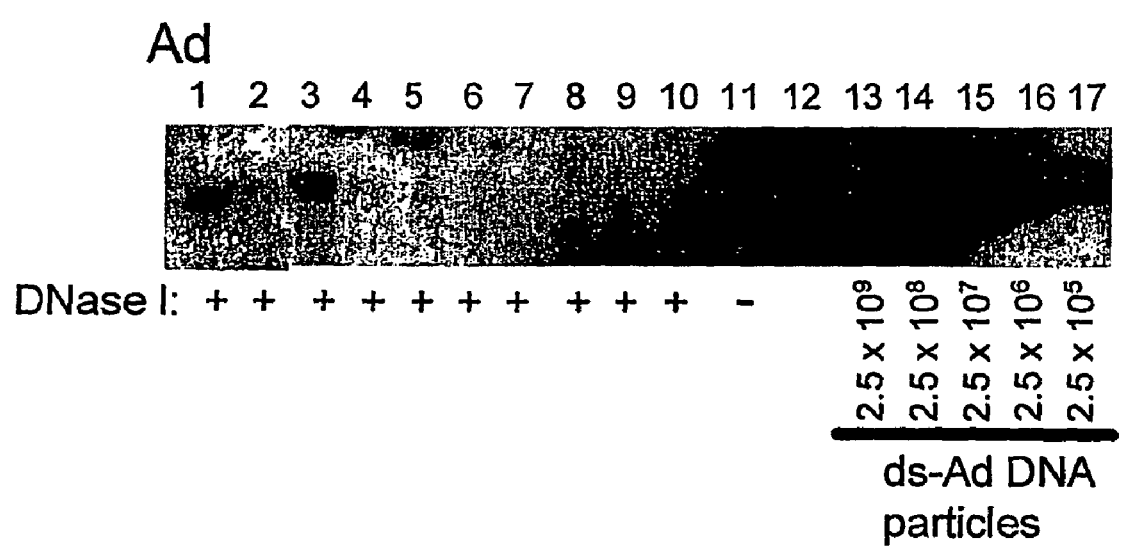
FIG. 3C is an autoradiograph of a Southern blot analysis that quantitated the contaminating Ad-AAV genomes in the samples described in FIG. 3B above. Lanes 10-18 differed as follows: (10) HA column ef 2 plus 2.5×10⁹ particles Ad-containing plasmid, (11) HA column ef 2 plus 2.5×10⁹ particles Ad-containing plasmid, no DNase I added, (12) No sample, (13)-(17) linearized Ad5-containing plasmid representing the indicated number of double-stranded (ds) Ad particles. The residual Ad-AAV in the AAV vector stock was reduced to less than 1 infectious particle per 10¹⁰ AAV vector particles.

AAV-CBGAApA was purified by the heparin-agarose column method (FIG. 3B) as described by Zolotukhin et al. (1999) *Gene Ther.* 6:973-985. AAV-CBGAApA DNase-I resistant particles were recovered efficiently from the 40% iodoxinal fraction (FIG. 3B, lane 2) by heparin-agarose column purification (FIG. 3B, lane 6). The signal for Ad-AAV in the vector preparation was reduced markedly by column purification of the AAV vector to less than the limit of detection (<0.5 Ad-AAV particle/cell), and even gross overexposure of the autoradiograph hybridized with an Ad5 probe did not reveal a signal for Ad-AAV genomes in the purified AAV vector stock (FIG. 3C, lane 1 versus lane 6). The DNase I-resistance of AAV vector particles was confirmed by the elimination of the signal for $2.5 \times 10^{10}$ added vector plasmid particles when DNase I was present (FIG. 2B, lane 10 versus lane 11).

Example 11 hGAA Expression with Ad-AAV and AAV Vectors in GAA-KO Mice

Figure 4A:
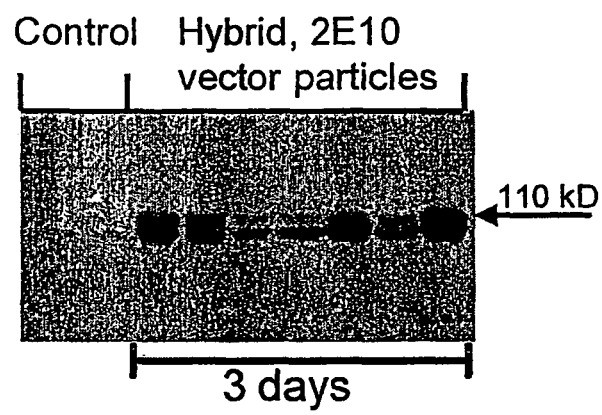
FIG. 4A depicts Western blot analysis of plasma that was performed at 3 days following intravenous administration of the hybrid Ad-AAV (essentially Ad) vector encoding hGAA (2×10¹⁰ vector particles/mouse). Recombinant hGAA (rhGAA) is shown for reference (2 ng total), and the ~110 kD hGAA precursor was detected as expected (Amalfitano et al. (1999) *Proc. Natl. Acad. Sci. U.S.A.* 96:8861-8866, Ding et al. (2001) *Hum. Gene Ther.* 12:955-965).

The hybrid Ad-AAV vector encoding hGAA was administered in vivo to demonstrate hGAA secretion as shown previously for a similar, modified Ad vector in GAA-KO mice (Amalfitano, A., et al. (1999) *Proc. Natl. Acad. Sci. USA* 96:8861-8866). The hybrid Ad-AAV vector encoding hGAA ($6 \times 10^{10}$ vector particles, according to quantitation by spectrophotometry (Ding et al. (2001) *Hum. Gene Ther.* 12:955-965)) was administered intravenously to GAA-KO mice. To allow comparison to experiments with AAV vectors, quantitation by Southern blot analysis revealed 3-fold fewer vector particles ($2 \times 10^{10}$ DNase I-resistant vector particles/GAA-KO mouse) than when the vector stock was quantified by spectroscopy. Secretion of hGAA was demonstrated in plasma by Western blot analysis on day 3 following vector administration (FIG. 4A); however, no hGAA was detected in plasma by Western blotting on day 7 following vector administration. The hGAA levels were sufficiently elevated in liver to generate detectable plasma levels of the ~110 kD precursor hGAA as have been reported for an Ad vector encoding hGAA (Amalfitano, A., et al. (1999) *Proc. Natl. Acad. Sci. USA* 96:8861-8866). The number of hybrid Ad-AAV vector particles administered was relatively low, indicating that higher systemic hGAA levels could be achieved by administration of higher numbers of vector particles (Amalfitano, A., et al. (1999) *Proc. Natl. Acad. Sci. USA* 96:8861-8866).

Figure 4B:
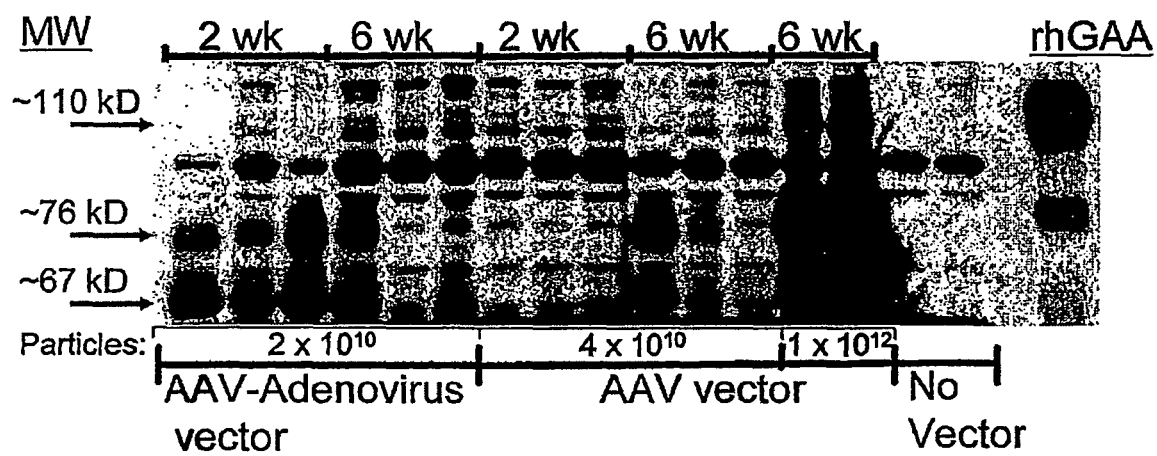
FIG. 4B depicts Western blot analysis of GAA-KO mice that received a hybrid Ad-AAV vector (2×10¹⁰ DNase I-resistant vector particles) or an AAV vector (4×10¹⁰ DNase I-resistant vector particles or 1×10¹² DNase I-resistant vector particles) encoding hGAA by intravenous administration. Western blot analysis of liver is shown at 2 and 6 weeks after vector administration for each group (n=3 for each group). (Note: hGAA in mouse liver migrates slightly faster than rhGAA.) GAA-KO mice that received an AAV vector (1×10¹² vector particles) encoding hGAA by intravenous administration (n=2) shown 6 weeks after vector administration. Untreated, affected GAA-KO mouse liver is shown for comparison (No vector, n=2). For the higher number of AAV vector particles, the ~67 kD, ~76 kD, and ~110 kD hGAA species were detected as expected (Amalfitano et al. (1999) *Proc. Nat. Acad. Sci. U.S.A.* 96:8861-8866, Ding et al. (2001) *Hum. Gene Ther.* 12:955-965).

AAV vector stocks were administered intravenously to GAA-KO mice for in vivo analysis of the AAV vector encoding hGAA. In order to deliver the same number of introduced genes encoding hGAA as mice that received the double-strand Ad-AAV vector, GAA-KO mice received twice as many (+ and − strand) single-stranded AAV vector genomes ($4 \times 10^{10}$ DNase I-resistant vector particles). No hGAA was detectable in plasma samples by Western blotting at 1, 2, or 6 weeks following administration of the AAV vector. The expression of hGAA in liver with Ad-AAV or the AAV vector was compared at 2 and 6 weeks following vector administration (FIG. 4B and Table 1). At 6 weeks the signal for hGAA with the lower dose of the AAV vector ($4 \times 10^{10}$ DNase I-resistant vector particle) was higher than for the hybrid Ad-AAV vector at the same time point (FIG. 4B; Table 2). Liver-targeted administration of a higher number of AAV vector particles ($1 \times 10^{12}$ DNase I-resistant vector particle/GAA-KO mouse) produced markedly higher levels of human GAA in liver at 6 weeks following vector adminstration than for a lower number of Ad-AAV or AAV vector particles (FIG. 4B; Table 2), approximately equivalent to the GAA level in wild-type mice (Ding et al. (2001) *Hum. Gene Ther.* 12:955-965).

TABLE 2

Enzyme analysis of GAA-KO mouse liver (nmol/hr/mg protein).

| Time following intravenous vector administration[1] | Ad-AAV[2], $2 \times 10^{10}$ (n = 3) | AAV[2], $4 \times 10^{10}$ (n = 3) | AAV[2], $1 \times 10^{12}$ (n = 2) |
|---|---|---|---|
| 2 weeks | 5.02 +/− 2.30 | 2.09 +/− 0.35 | Not done |
| 6 weeks | 1.55 +/− 0.48 | 3.07 +/− 0.77 | 71.28 +/− 2.60 |

[1]hGAA in age-matched, 3 month-old GAA-KO mouse liver = 1.35 +/− 0.15 (n = 2)
[2]Ad-AAV-CBGAApA, hybrid Ad-AAV vector (DNase I-resistant particles)
[3]AAV-CBGAApA, AAV vector (DNase I-resistant particles)

Example 12

Long-Term Correction Of Glycogen Storage Disease, Type II, With A Hybrid Adeno-Associated Virus-Adenovirus (Ad-AAV) Hybrid Vector A replication-defective Ad-AAV hybrid virus was developed, and was evaluated in muscle-targeted gene therapy in glycogen storage disease type II (GSD II). Patients with GSD II exhibit a progressive myopathy related to glycogen storage, that ultimately leads to death from cardiac or respiratory failure. In the Ad-AAV hybrid vector the AAV vector sequence has been cloned into an E1, polymerase/preterminal protein-deleted adenovirus, such that it is packaged as an adenovirus vector. The AAV vector sequence contains a human acid glucosidase (hGAA) cDNA driven by a hybrid CMV-chicken β-actin promoter. The hybrid was administered to acid glucosidase-knockout (GAA-KO) mice on day 3 of life by gastrocnemius injection. Subsequently the glycogen content and hGAA levels were analyzed in skeletal muscles, heart, diaphragm and liver at various time points. The muscles of the hindlimb showed reduced glycogen content and persistent hGAA for up to 6 months following vector administration. Vector RNA was detected by Northern blot analysis of the hindlimb muscles for up to 6 months. Vector RNA and hGAA were present in the heart for 3 of 13 GAA-KO mice for up to 6 months. Surprisingly, an antibody response to hGAA was found in 10 of 13 mice; moreover, vector DNA and RNA and hGAA persisted at low levels in the hearts of 3 GAA-KO mice that did not exhibit an antibody response to hGAA. The presence of antibodies against hGAA did not reverse the correction of glycogen storage in the skeletal muscle of GAA-KO mice, implying that gene therapy has a potential beneficial effect in patients with inhibitor antibodies that would preclude successful enzyme therapy.

Example 13 hGAA Expression with AAV6 Vectors in GAA-KO Mice

The AAV2 pseudotyped vector detailed above demonstrated wild-type levels of hGAA expression after muscle-targeted delivery in GAA-knockout mice, and glycogen content was reduced in transduced muscle signifying a partial correction of GSD II. To increase hGAA expression of the introduced gene in muscle, the AAV vector was subsequently packaged with AAV6 capsids utilizing the hybrid AD-AAV method. The hybrid Ad-AAV method achieved approximately 100-fold higher packaging efficiency of the AAV6 pseudotyped vector as compared to the transfection-only method, approximately 7000 DNase-I resistant particles/cell. The AAV6 pseudotyped vector is targeted to muscle in the GAA-KO mouse, and the levels of hGAA expression for that vector are compared to the AAV2 pseudotyped vector. AAV1 pseudotyped vectors produced much higher levels of introduced proteins than AAV2 pseudotyped vectors in muscle, and AAV6 capsids are essentially identical to AAV1 capsids. Therefore, much improved hGAA expression for the AAV6 pseudotyped vector in muscle is likely, and further development of Ad-AAV and AAV vectors encoding hGAA offers distinct advantages for gene therapy in GSD II.

Example 14 hGAA Secretion Following Portal Vein Injection With AAV Vectors In GAA-KO/SCID Mice In order to maximize the transduction of liver with the AAV vector and increase the likelihood of secretion of hGAA, the AAV vector was delivered by portal vein injection in GAA-KO/SCID mice. Anti-hGAA antibodies previously abbreviated the secretion of hGAA with Ad vectors in the liver of GAA-KO mice, and anti-hGAA antibodies were not expected after vector administration in GAA-KO/SCID mice (Ding, E. Y., et al. (2001), *Hum. Gene Ther.* 12:955-965). Western blot analysis of plasma demonstrated hGAA at 2 and 4 weeks following portal vein administration of AAV-CBGAApA packaged either as AAV2 or as AAV6 (FIG. 5A), and was still detected 3 months following injection of the AAV vector. Liver production of hGAA was elevated approximately 10-fold compared to wild-type levels (1110+/−120 mm/mg/hr) for a GAA-KO/SCID mouse at 3 months following AAV2 vector administration. For the vector pseudotyped as AAV6, hGAA was elevated approximately twice the level seen in normal mice. Untreated GAA-KO/SCID control mice had low GAA activity in liver (1.4+/−0.3 mm/mg/hr).

Figure 5:
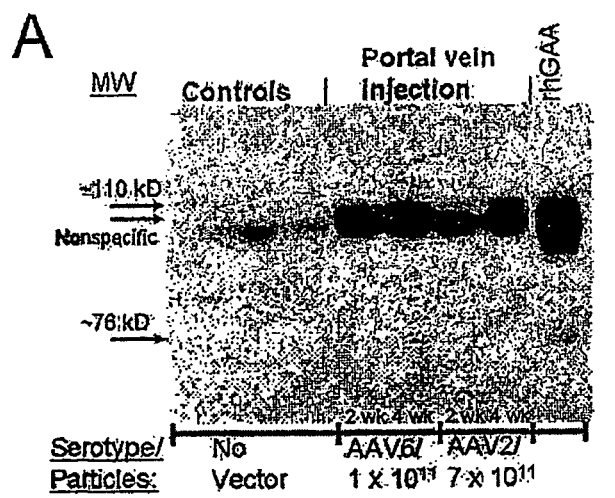
FIGS. 5A-5C depict human GAA secretion and uptake following portal vein injection of an AAV vector in GAA-KO mice.
Figure 5:
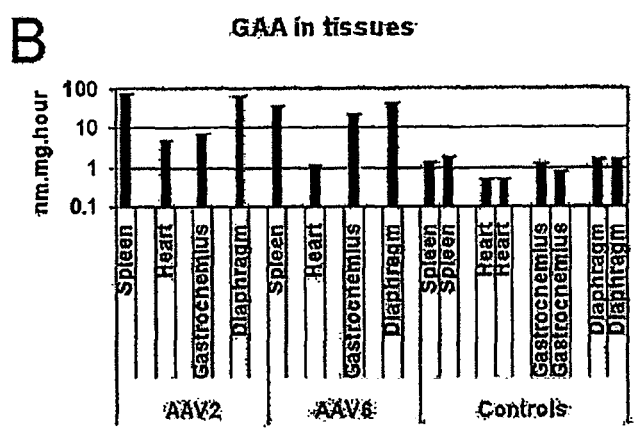
Figure 5:
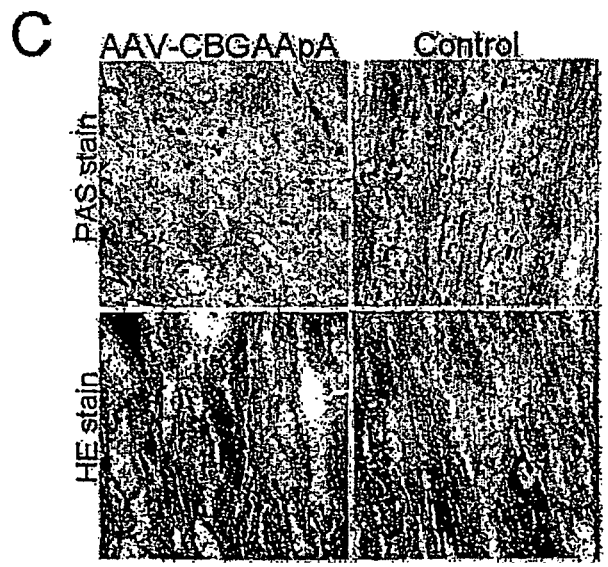

Distal uptake of hGAA at the 3-month time point was demonstrated in mice by GAA analysis of spleen, heart, diaphragm, and the gastrocnemius, where GAA was clearly above the background activity for untreated, GAA-KO/SCID mice (FIG. 5B). An advantage from hGAA delivery to the heart, a primary site of pathology in infantile GSD II (also known as Pompe disease) was shown by reduced glycogen staining for the mouse that received the AAV2 vector, as compared to an untreated control (FIG. 5C). Furthermore, glycogen content in heart was reduced to 0.21 mmol glucose/gram protein (range 0.14 to 0.28), compared to 1.2+/−0.25 mmol glucose/gm protein for untreated controls.

It will be understood that various details of the invention can be changed without departing from the scope of the invention. Furthermore, the foregoing description is for the purpose of illustration only, and not for the purpose of limitation.

What is claimed is:

1. A recombinant hybrid virus, comprising:
   (a) a deleted adenovirus vector genome comprising the adenovirus 5' and 3' cis-elements for viral replication and encapsidation; a functional adenovirus genomic region selected from the group consisting of an adenovirus E1a region, E2a region, E4orf6 region, VA RNA region, and any combination of the foregoing; and further comprising a deletion in an adenovirus genomic region selected from the group consisting of:
      (i) the polymerase region, wherein said deletion essentially prevents the expression of a functional polymerase protein from said deleted region and said hybrid virus does not otherwise express a functional polymerase protein,
      (ii) the preterminal protein region, wherein said deletion essentially prevents the expression of a functional preterminal protein from said deleted region, and said hybrid virus does not otherwise express a functional preterminal protein, and
      (iii) both the regions of (i) and (ii); and
   (b) a recombinant adeno-associated virus (AAV) vector genome flanked by the adenovirus vector genome sequences of (a), said recombinant AAV vector genome comprising (i) AAV 5' and 3' inverted terminal repeats, (ii) an AAV packaging sequence, and (iii) a heterologous nucleic acid sequence, wherein said heterologous nucleic acid sequence is flanked by the 5' and 3' AAV inverted terminal repeats of (i), and further wherein the AAV vector genome does not encode the AVV Rep or AAV capsid proteins,
   wherein upon infection of a 293 helper cell line, the recombinant hybrid virus is packaged into an AVV particle essentially without producing contaminating adenovirus.

2. The recombinant hybrid virus of claim 1, wherein said adenovirus 5' and 3' cis-elements comprise 5' and 3' adenovirus inverted terminal repeats and an adenovirus packaging sequence.

3. The recombinant hybrid virus of claim 1, wherein said AAV inverted terminal repeats are selected from the group consisting of AAV-1, AAV-2, AAV-3, AAV-4, AAV-5 and AAV-6 inverted terminal repeats.

4. The recombinant hybrid virus of claim 1, wherein said adenovirus vector genome comprises sequences encoding an AAV Rep protein.

5. The recombinant hybrid virus of claim 4, wherein said sequences encoding said AAV Rep protein are operably associated with an inducible promoter.

6. The recombinant hybrid virus of claim 5, wherein said inducible promoter is selected from the group consisting of a tetracycline response element, an ecdysone response element, a heat shock promoter, an MMLV long terminal repeat sequence, a bacteria phage T7 promoter, a metallothionein response element, and the AAV p5 promoter.

7. The recombinant hybrid virus of claim 4, wherein said sequences encoding said AAV Rep protein are operably associated with a promoter selected from the group consisting of a liver-specific promoter, a muscle-specific promoter, and a brain-specific promoter.

8. The recombinant hybrid virus of claim 1, wherein said adenovirus vector genome comprises sequences encoding an AAV capsid protein.

9. The recombinant hybrid virus of claim 1, wherein said adenovirus vector genome further comprises a deletion in an adenovirus region selected from the group consisting of the Iva2 region, the 100K region, the E3 region, the E2a region, the E4 region, the L1 region, the L2 region, the L3 region, the L4 region, the L5 region, the intermediate gene IX region, and any combination of the foregoing, wherein said adenovirus vector genome does not otherwise express a gene product associated with the deleted region.

10. The recombinant hybrid virus of claim 1, wherein said adenovirus vector genome comprises a deletion in the preterminal protein region.

11. The recombinant hybrid virus of claim 10, wherein said deletion comprises a deletion in the preterminal protein region at about nucleotides 9198 to 9630 of the adenovirus serotype 5 genome or a corresponding region of the genome of an adenovirus of another serotype.

12. The recombinant hybrid virus of claim 1, wherein said deletion comprises a deletion in the polymerase region.

13. The recombinant hybrid virus of claim 12, wherein said deletion in said polymerase region comprises a deletion at about nucleotides 7274 to 7881 of the adenovirus serotype 5 genome or a corresponding region of the genome of an adenovirus of another serotype.

14. The recombinant hybrid virus of claim 1, wherein said heterologous nucleic acid sequence is operatively associated with an expression control sequence.

15. The recombinant hybrid virus of claim 14, wherein said expression control sequence comprises a promoter.

16. The recombinant hybrid virus of claim 15, wherein said promoter is selected from the group consisting of a liver-specific promoter, a muscle-specific promoter, a brain-specific promoter, and a glucose-responsive promoter.

17. The recombinant hybrid virus of claim 15, wherein said promoter is an inducible promoter.

18. The recombinant hybrid virus of claim 15, wherein said promoter is selected from the group consisting of the CMV promoter, albumin promoter, EF1-α promoter, PγK promoter, MFG promoter, and Rous sarcoma virus promoter.

19. The recombinant hybrid virus of claim 1, wherein said heterologous nucleic acid sequence encodes a polypeptide.

20. The recombinant hybrid virus of claim 19, wherein said polypeptide is selected from the group consisting of a therapeutic polypeptide, an immunogenic polypeptide, and a reporter polypeptide.

21. The recombinant hybrid virus of claim 20, wherein said polypeptide is associated with a lysosomal storage disease.

22. The recombinant hybrid virus of claim 21, wherein said polypeptide is selected from the group consisting of β-galactosidase, β-hexosaminidase A, β-hexosaminidase B, $GM_2$ activator protein, glucocerebrosidase, arylsulfatase A, galactosylceramidase, acid sphingomyelinase, acid ceramidase, acid lipase, α-L-iduronidase, iduronate sulfatase, heparan N-sulfatase, α-N-acetylglucosaminidase acetyl-CoA, glucosaminide acetyltransferase, N-acetylglucosamine-6-sulfatase, arylsulfatase B, β-glucuronidase, α-mannosidase, β-mannosidase, α-L-fucosidase, N-aspartyl-β-glucosaminidase, α-neuraminidase, lysosomal protective protein, α-N-acetyl-galactosaminidase, N-acetylglucosamine-1-phosphotransferase, cystine transport protein, sialic acid transport protein, the CLN3 gene product, palmitoyl-protein thioesterase, saposin A, saposin B, saposin C, and saposin D.

23. The recombinant hybrid virus of claim 19, wherein said polypeptide is associated with a glycogen storage disease.

24. The recombinant hybrid virus of claim 23, wherein said polypeptide is selected from the group consisting of glucose 6-phosphatase, lysosomal acid α glucosidase, glycogen debranching enzyme, branching enzyme, muscle phosphorylase, liver phosphorylase, phosphorylase kinase, muscle phosphofructokinase, glycogen synthase, phosphoglucoisomerase, muscle phosphoglycerate kinase, phosphoglycerate mutase, and lactate dehydrogenase.

25. The recombinant hybrid virus of claim 24, wherein said polypeptide is a lysosomal acid α-glucosidase.

26. The recombinant hybrid virus of claim 25, wherein said polypeptide is a human lysosomal acid α-glucosidase.

27. The recombinant hybrid virus of claim 1, wherein said heterologous nucleic acid sequence encodes an antisense nucleic acid sequence.

28. A hybrid virus particle comprising the recombinant hybrid virus of claim 1 encapsidated within an adenovirus capsid.

29. A cell comprising the recombinant hybrid virus of claim 1 or the hybrid virus particle of claim 28.

30. A method of producing a recombinant adeno-associated virus (AAV) particle, comprising providing to a cell:
a recombinant hybrid virus according to claim 1 or a hybrid virus particle according to claim 28;
(b) AAV sequences sufficient for replication and packaging of the AAV vector genome; and
(c) AAV sequences sufficient to produce a functional AAV capsid, wherein (a), (b) and (c) are provided to the cell under conditions sufficient for replication of the AAV vector genome and packaging thereof in the AAV capsid such that AAV particles comprising the AAV vector genome encapsidated within the AAV capsid are produced in the cell.

31. The method of claim 30, further comprising the step of collecting the recombinant AAV particle.

32. The method of claim 30, further comprising providing to the cell the adenovirus helper functions for AAV replication and packaging.

33. The method of claim 32, wherein adenovirus E1a, E2a, E4orf6, and VA RNA helper sequences are provided.

34. The method of claim 30, wherein the cell is selected from the group consisting of a HeLa cell, a 293 cell, a muscle cell, and a liver cell.

35. The method of claim 30, wherein essentially no adenovirus particles are produced.

36. The method of claim 30, wherein the yield of recombinant AAV particles is at least 5-fold greater than in the presence of the adenovirus polymerase and/or preterminal proteins.

37. The method of claim 30, wherein sequences encoding an AAV Rep protein and/or sequences encoding the AAV capsid protein are stably expressed by the cell.

38. The method of claim 30, wherein sequences encoding an AAV Rep protein and/or sequences encoding the AAV capsid protein are provided by a vector other than the recombinant hybrid virus.

39. The method of claim 38, wherein the vector is selected from the group consisting of a plasmid, an adenovirus, an Epstein Barr virus, and a herpesvirus vector.

40. The method of claim 30, wherein the AAV inverted terminal repeats and the AAV capsid are derived from different AAV serotypes.

41. The method of claim 30, wherein the AAV capsid is an AAV-6 capsid.

42. The method of claim 30 or claim 41, wherein the AAV inverted terminal repeats are AAV-2 inverted terminal repeats.

43. A method of producing a recombinant adeno-associated virus (AAV) particle, comprising providing to a cell a hybrid virus particle according to claim 28, said recombinant hybrid virus particle expressing the adenovirus helper functions for AAV replication and packaging; wherein the cell (i) expresses AVV rep sequences sufficient for replication and packaging of the AAV vector genome, (ii) expresses AAV cap sequences sufficient to produce a functional AAV capsid, and (iii) does not express sequences sufficient to produce a functional adenovirus E1a protein; and further wherein the hybrid virus particle is provided under conditions sufficient for replication of the AAV vector genome and packaging thereof in the AVV capsid such that AAV particles comprising the AAV vector genome encapsidated within the AAV capsid are produced in the cell.

44. A method of producing a recombinant adeno-associated virus (AVV) particle, comprising providing to a cell a hybrid virus particle according to claim 28, the hybrid virus particle expressing:
(i) adenovirus helper functions for AAV replication and packaging except the hybrid virus particle does not express a functional adenovirus E1a gene product,
(ii) AAV rep sequences sufficient for replication and packaging of the AVV vector genome, and
(iii) AVV cap sequences sufficient to produce a functional AAV capsid,
wherein the cell expresses functional adenovirus E1a gene products; and further wherein the hybrid virus particle is provided to the cell under conditions sufficient for replication of the AAV vector genome and packaging thereof in the AVV capsid such that AVV particles comprising the AAV vector genome encapsidated within the AAV capsid are produced in the cell.

45. A method of producing a recombinant adeno-associated virus (AAV) particle, comprising providing to a cell:
   a hybrid virus particle according to claim 28, the hybrid virus particle expressing adenovirus helper functions for AVV replication and packaging except the hybrid virus particle does not express a functional adenovirus E1a gene product,
   (b) a separate vector comprising inducible AAV rep sequences sufficient for replication and packaging of the AAV vector genome, and AAV cap sequences sufficient to produce a functional AVV capsid,
   wherein the cell expresses a functional adenovirus E1a gene product; and further wherein (a) and (b) are provided to the cell under conditions sufficient for replication of the AVV vector genome and packaging thereof in the AAV capsid such that AAV particles comprising the AAV vector genome encapsidated within the AAV capsid are produced in the cell.

46. A method of producing a recombinant adeno-associated virus (AAV) particle, comprising providing to a cell:
   (a) a hybrid virus particle according to claim 28, the hybrid virus particle expressing adenovirus helper functions for AAV replication and packaging,
   (b) a separate vector comprising AAV rep sequences sufficient for replication and packaging of the AAV vector genome, and AAV cap sequences sufficient to produce a functional AAV capsid,
   wherein the cell does not express a functional adenovirus E1a gene product; and further wherein (a) and (b) are provided to the cell under conditions sufficient for replication of the AAV vector genome and packaging thereof in the AAV capsid such that AAV particles comprising the AAV vector genome encapsidated within the AAV capsid are produced in the cell.

47. The method of claim 45 or claim 46, wherein the separate vector is a plasmid vector.

48. The method of claim 45 or claim 46, wherein the separate vector is an adenovirus vector.

49. A method of introducing a nucleic acid into a cell, comprising contacting a cell with the recombinant hybrid virus of claim 1 or the hybrid virus particle of claim 28 under conditions sufficient for entry of the recombinant virus particle into the cell.

50. The method of claim 49, wherein the cell is selected from the group consisting of a neuron, a brain cell, a retinal cell, an epithelial cell, a cardiac muscle cell, a smooth muscle cell, a skeletal muscle cell, a diaphragm muscle cell, a pancreatic cell, a liver cell, a fibroblast, an endothelial cell, a germ cell, a lung cell, a prostate cell, a stem cell, a progenitor cell, and a cancer cell.

51. The method of claim 49, wherein the cell is a mammalian cell.

52. The method of claim 49, further comprising introducing an AAV Rep 68/78 protein or sequences encoding an AAV Rep 68/78 protein into the cell.

53. The recombinant hybrid virus of claim 1, wherein the deleted adenovirus vector genome further comprises a functional adenovirus E1a region.

54. A recombinant cell comprising the recombinant hybrid virus of claim 1, wherein the recombinant cell is stably modified to express a functional pol polypeptide, a functional pTP polypeptide, or both.

55. A recombinant hybrid virus, comprising:
   (a) a deleted adenovirus vector genome comprising:
      (i) the adenovirus 5' and 3' cis-elements for viral replication and encapsidation;
      (ii) a functional E1a region and at least one additional functional adenovirus genomic region selected from the group consisting of an adenovirus E2a region, an adenovirus E4orf6 region, and an adenovirus VA RNA region; and
      (iii) a deletion in an adenovirus genomic region, wherein the deletion essentially prevents the expression of a functional polymerase protein, a functional preterminal protein, or both from the adenovirus genomic region, and further wherein said hybrid virus does not otherwise express a functional polymerase protein, a functional preterminal protein, or both; and
   (b) a recombinant adeno-associated virus (AAV) vector genome flanked by the adenovirus vector genome sequences of (a), said recombinant AAV vector genome comprising:
      (iv) a heterologous nucleic acid sequence flanked by AAV 5' and 3' inverted terminal repeats;
      (v) an AAV packaging sequence; and
      (vi) a deletion of the AAV Rep region, the AAV Cap region, or both, such that the recombinant AAV vector genome does not encode a functional AVV Rep polypeptide, a functional AAV capsid polypeptide, or both,
   wherein upon infection of a 293 helper cell line, the recombinant hybrid virus is packaged into an AAV particle essentially without producing contaminating adenovirus.

56. A hybrid virus particle comprising the recombinant hybrid virus of claim 55 encapsidated within an adenovirus capsid.

57. An adeno-associated virus (AAV) particle produced by introducing the hybrid virus particle of claim 56 into a cell that expresses AVV Rep and AAV Cap.

58. A recombinant cell comprising the recombinant hybrid virus of claim 55, wherein the recombinant cell is stably modified to express a functional pol polypeptide, a functional pTP polypeptide, or both.

* * * * *